(12) United States Patent
Zhang et al.

(10) Patent No.: US 10,562,904 B2
(45) Date of Patent: Feb. 18, 2020

(54) SYNTHESIS PROCESS OF RUXOLITINIB

(71) Applicant: CHIA TAI TIANQING PHARMACEUTICAL GROUP CO., LTD., Lianyungang (CN)

(72) Inventors: Xiquan Zhang, Lianyungang (CN); Aiming Zhang, Lianyungang (CN); Zhou Zhou, Lianyungang (CN); Leilei Yang, Lianyungang (CN); Huadong Yao, Lianyungang (CN); Xueyan Zhu, Lianyungang (CN); Hubo Wang, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/066,482

(22) PCT Filed: Dec. 29, 2016

(86) PCT No.: PCT/CN2016/113000
§ 371 (c)(1),
(2) Date: Jun. 27, 2018

(87) PCT Pub. No.: WO2017/114461
PCT Pub. Date: Jul. 6, 2017

(65) Prior Publication Data
US 2019/0023712 A1    Jan. 24, 2019

(30) Foreign Application Priority Data
Dec. 31, 2015    (CN) .......................... 2015 1 1028724

(51) Int. Cl.
*C07D 487/04* (2006.01)
*A61K 31/519* (2006.01)
*C07D 231/08* (2006.01)
*C07F 7/10* (2006.01)

(52) U.S. Cl.
CPC ......... *C07D 487/04* (2013.01); *C07D 231/08* (2013.01); *C07F 7/10* (2013.01); *Y02P 20/55* (2015.11)

(58) Field of Classification Search
CPC .................................................. C07D 487/04
See application file for complete search history.

(56) References Cited

U.S. PATENT DOCUMENTS

| | | | | |
|---|---|---|---|---|
| 7,517,910 B2* | 4/2009 | Yasuma | ............... | A61K 31/381 514/569 |
| 7,880,009 B2* | 2/2011 | Kimura | ............... | C07D 401/10 546/210 |
| 8,410,265 B2* | 4/2013 | Zhou | ................... | C07D 487/04 544/280 |

FOREIGN PATENT DOCUMENTS

| | | |
|---|---|---|
| CN | 101448826 A | 6/2009 |
| CN | 102348693 A | 2/2012 |
| WO | 2007070514 A1 | 6/2007 |
| WO | 2010039939 A1 | 4/2010 |

(Continued)

OTHER PUBLICATIONS

Valeur et al. Chem. Soc. Rev., 2009, 38, 606-631 (Year: 2009).*

(Continued)

*Primary Examiner* — Emily A Bernhardt
(74) *Attorney, Agent, or Firm* — Kilpatrick Townsend & Stockton LLP

(57) ABSTRACT

The present application falls within the field of drug synthesis, and in particular, the present application relates to a method for preparing ruxolitinib, and a method for preparing the intermediate and relevant intermediates used. The method comprises reacting a compound of formula II with a compound of formula IV or a salt thereof to obtain a compound of formula III, and then subjecting the compound of formula III to an acyl halogenation reaction, an amidation reaction, and a reaction dehydrating an amide to form a cyano group or removing the protecting group to prepare ruxolitinib. The method has the characteristics of brief steps, a high stereoselectivity, a high utilization ratio of atoms, mild reaction conditions and convenient post treatment. The method avoids using expensive asymmetric reaction catalysts, and is suitable for industrial production.

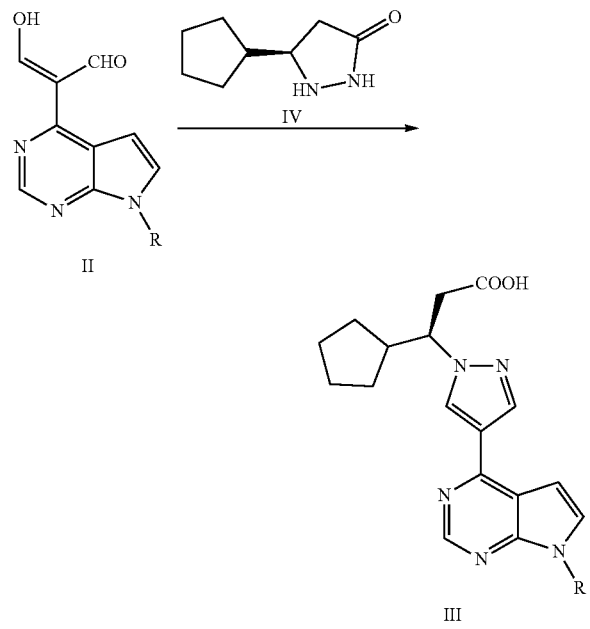

20 Claims, No Drawings

(56) References Cited

FOREIGN PATENT DOCUMENTS

WO    2010/083283  A2    7/2010
WO     2010116282  A1   10/2010

OTHER PUBLICATIONS

Li, Wenjie, et al. "Synthesis of High Optical Purity," Chinese Journal of Synthetic Chemistry, vol. 19, No. 2, Feb. 28, 2011 (Feb. 28, 2011), pp. 280-282.
International Search Report dated Mar. 30, 2017 in International Patent Application No. PCT/CN2016/113000, 6 pages.
Search Report in CN201680072360X, dated Sep. 5, 2019.
Casimiro-Garcia, et al. "Identification of (R)-6-(1-(4-Cyano-3-methylphenyl)-5-cyclopentyl-4, 5-dihydro-1 H-pyrazol-3-yl)-2-methoxynicotinic Acid, a Highly Potent and Selective Nonsteroidal Mineralocorticoid Receptor Antagonist." Journal of medicinal chemistry 57, No. 10 (2014): 4273-4288.
"Organic Synthesis," Zhu Bin (editor), Southwest Jiaotong University Press, Jan. 2014, ISBN 978-7-5643-2577-0.
Chinese Office Action in CN201680072360X, dated Sep. 16, 2019, 5 pages.

* cited by examiner

SYNTHESIS PROCESS OF RUXOLITINIB

CROSS REFERENCE TO RELATED APPLICATION

The present application is a U.S. National Phase application under 35 U.S.C. § 371 of International Application No. PCT/CN2016/113000, filed Dec. 29, 2016, which claims priority to and the benefit of the Chinese patent application No. 201511028724.8 filed with the State Intellectual Property Office of China on Dec. 31, 2015, the disclosures of which are incorporated herein by reference in their entireties.

TECHNICAL FIELD

The present application belongs to the field of pharmaceutical synthesis. Specifically, the present application relates to a method for preparing ruxolitinib, intermediates used therein, and methods for preparing related intermediates.

BACKGROUND

Ruxolitinib is a selective JAK1/JAK2 tyrosine kinase inhibitor developed cooperatively by Incyte Corporation and Novartis Corporation. It is the first drug (Trade name: Jakafi) approved by the US FDA in November 2011 for the treatment of myelofibrosis, and indications thereof are intermediate or high-risk myelofibrosis, including primary myelofibrosis, secondary polycythemia myelofibrosis and post-essential thrombocythemia myelofibrosis. New indications approved by FDA in December 2014 are polycythemia vera with an inadequate response to or intolerance of semicarbazide. In August 2012, it was approved for marketing by the European Union (Trade name: Jakavi); and in July 2014, it was approved for marketing in Japan.

The chemical name of ruxolitinib is (R)-3-cyclopentyl-3-(4-(7H-pyrrolo[2,3-d]pyrimidin-4-yl)-1H-pyrazol-1-yl)propanenitrile, and its structural formula is shown in Formula I:

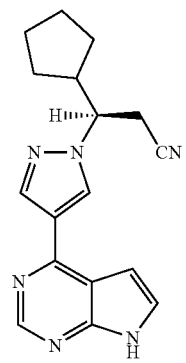

I

WO2007070514, WO2010039939, WO2010116282, US20090181959 and Org Lett, 2009, 10(9): 1999-2002 respectively disclose the methods for preparing ruxolitinib and related intermediates, and Drugs of the Future (2010), 35(6), 457-465 provides a review of the above disclosed methods. In the route disclosed in the review, the chiral resolution is set close to the step of forming a final product, and the atomic utilization rate is relatively low and the cost is relatively high. Moreover, the structure of the chiral catalyst is relatively complex and the amount of the catalyst used therein is relatively high. The ee value of the product obtained by chiral resolution is not high, the chiral purity can only reach about 90%, and the product still needs to be resolved or subject to a multi-step refining process to obtain a product with medicinal value.

Angew. Chem. Int. Ed. 2015, 54, 7149-7153 discloses another method for preparing ruxolitinib, in which the amounts of rhodium catalyst and its metal ligand used therein are relatively high and the reaction conditions are harsh. This method is not conducive to large-scale production in view of cost and operation.

In order to overcome the shortcomings of the synthesis processes as described above, the present application aims to provide a new method for preparing ruxolitinib, which is suitable for industrial production.

SUMMARY OF THE INVENTION

In one aspect, the present application provides a process for preparing ruxolitinib, the compound of Formula I, comprising the following steps:

Step 4: converting a compound of Formula III into a compound of Formula XI, and then converting the compound of Formula XI into a compound of Formula XII in the presence of an aminating agent,

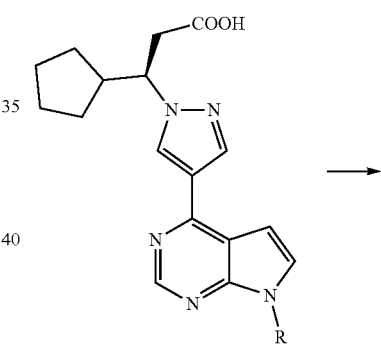

III

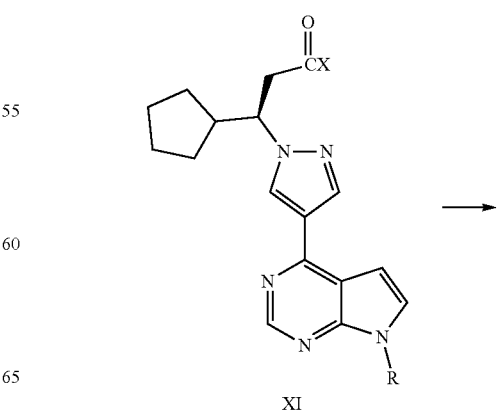

XI

-continued

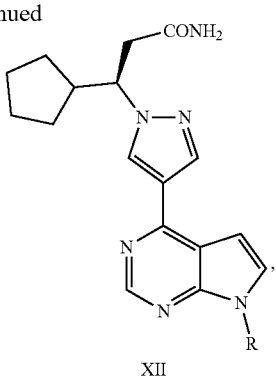

XII wherein R is selected from H and an amino-protecting group, and X is selected from Cl and Br; and Step 5-1: where R is H, converting the acylamino group in Formula XII into a cyano group in the presence of a dehydrating agent to obtain ruxolitinib, the compound of Formula I; or Step 5-2: where R is an amino-protecting group, converting the acylamino group in Formula XII into a cyano group and removing the amino-protecting group R to obtain ruxolitinib, the compound of Formula I,

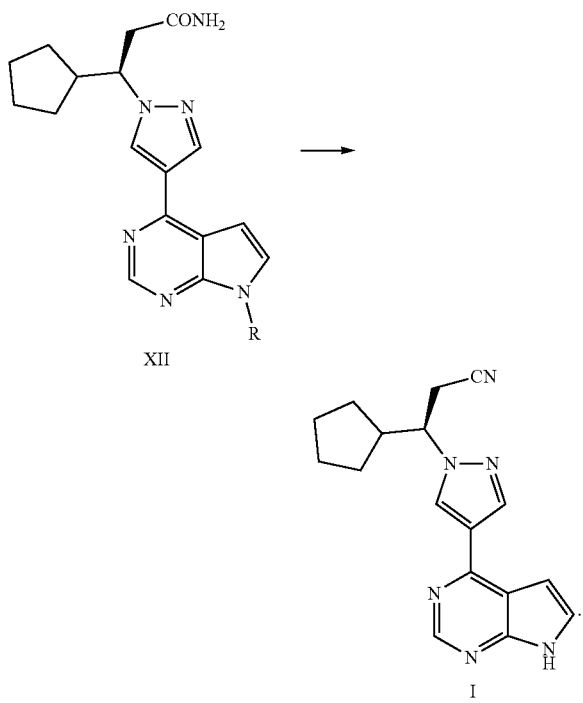

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the reagent used in the reaction of converting the compound of Formula III into the compound of Formula XI in Step 4 is selected from one or more of phosphorus trichloride, phosphorus pentachloride, thionyl chloride and oxalyl chloride, preferably oxalyl chloride.

In some embodiments of the present application, the solvent used in the reaction of converting the compound of Formula III into the compound of Formula XI in Step 4 is selected from tetrahydrofuran, dichloromethane, trichloromethane, chlorobenzene, acetonitrile, DMA, NMP, ethyl acetate, isopropyl acetate, toluene, xylene, and a mixed solvent of more than one of the above solvents, preferably NMP or dichloromethane, or a mixed solvent thereof.

In some embodiments of the present application, the aminating agent used in the reaction of converting the compound of Formula XI into the compound of Formula XII in Step 4 is selected from one or more of aqueous ammonia, liquid ammonia, and ammonia gas, preferably aqueous ammonia.

In some embodiments of the present application, the solvent used in the reaction of converting the compound of Formula XI into the compound of Formula XII in Step 4 is selected from tetrahydrofuran, dichloromethane, trichloromethane, chlorobenzene, acetonitrile, DMA, NMP, ethyl acetate, isopropyl acetate, toluene, xylene, and a mixed solvent of more than one of the above solvents, preferably dichloromethane or tetrahydrofuran, or a mixed solvent thereof.

In some embodiments of the present application, the dehydrating agent used in Step 5-1 is selected from one or more of phosphorus oxychloride, cyanuric chloride, phosphorus pentoxide, thionyl chloride, trifluoroacetic anhydride, trifluoro sulfonic anhydride and oxalyl chloride, preferably phosphorus oxychloride or cyanuric chloride.

In some embodiments of the present application, the solvent used in Step 5-1 is selected from tetrahydrofuran, dichloromethane, trichloromethane, chlorobenzene, acetonitrile, DMA, NMP, DMSO, ethyl acetate, isopropyl acetate, toluene, xylene, and a mixed solvent of more than one of the above solvents, preferably dichloromethane or NMP, or a mixed solvent thereof.

In some embodiments of the present application, the molar ratio of the compound of Formula XII to the dehydrating agent in Step 5-1 is 1:1~10, preferably 1:3~8, more preferably 1:4~7, and further preferably 1:5~7.

In the present application, the order of the reaction of converting the acylamino group in Formula XII into a cyano group and the reaction of removing the amino-protecting group R in Step 5-2 may be changed. For example, when preparing ruxolitinib from the compound of Formula XII (R=amino-protecting group), the reaction of converting the acylamino group into a cyano group may be performed firstly and then the reaction of removing the protecting group R is performed, or the reaction of removing the protecting group R may be performed firstly and then the reaction of converting the acylamino group into a cyano group is performed, both of which are within the protection scope of the present application.

In some embodiments of the present application, the dehydrating agent used in the reaction of converting the acylamino group into a cyano group in Step 5-2 is selected from one or more of phosphorus oxychloride, cyanuric chloride, phosphorus pentoxide, thionyl chloride, trifluoroacetic anhydride, trifluoro sulfonic anhydride and oxalyl chloride, preferably phosphorus oxychloride or cyanuric chloride.

In some embodiments of the present application, the solvent used in the reaction of converting the acylamino group into a cyano group in Step 5-2 is selected from tetrahydrofuran, dichloromethane, trichloromethane, chlorobenzene, acetonitrile, DMA, NMP, DMSO, ethyl acetate, isopropyl acetate, toluene and xylene, preferably dichloromethane or NMP.

In some embodiments of the present application, the acylamino group is converted into a cyano group in the presence of a dehydrating agent in Step 5-2, wherein the molar ratio of the compound of Formula XII (R=amino-protecting group) to the dehydrating agent is 1:1~10, preferably 1:3~8, more preferably 1:4~7, and further preferably 1:5~7.

In some embodiments of the present application, the reaction of removing the protecting group R in Step 5-2 may be performed under an acidic or basic condition. Under an acidic or basic condition, the reaction of removing the protecting group R may be performed by selecting an appropriate catalyst and solvent.

In some embodiments of the present application, under an acidic condition, the catalyst used in the reaction of removing the protecting group R in Step 5-2 is selected from trifluoroacetic acid, trifluoroacetic anhydride, lithium tetrafluoroborate and boron trifluoride-diethyl etherate, preferably trifluoroacetic acid or boron trifluoride-diethyl etherate.

In some embodiments of the present application, under an acidic condition, the solvent used in the reaction of removing the protecting group R in Step 5-2 is selected from dichloromethane, tetrahydrofuran, acetonitrile, water, NMP, DMA and DMF, preferably acetonitrile or NMP.

In some embodiments of the present application, under a basic condition, the catalyst used in the reaction of removing the protecting group R in Step 5-2 is selected from sodium carbonate, cesium carbonate, potassium carbonate, sodium hydroxide, potassium hydroxide, lithium hydroxide, potassium tert-butoxide, sodium tert-butoxide, hydrazine hydrate and tetrabutylammonium fluoride, preferably lithium hydroxide or potassium carbonate.

In some embodiments of the present application, under a basic condition, the solvent used in the reaction of removing the protecting group R in Step 5-2 is selected from ethanol, water, methanol, tetrahydrofuran and isopropanol, preferably water or tetrahydrofuran.

In some embodiments of the present application, the process for preparing ruxolitinib, the compound of Formula I, according to the present application optionally further comprises Step 3: reacting a compound of Formula II with a compound of Formula IV or a salt thereof to obtain the compound of Formula III,

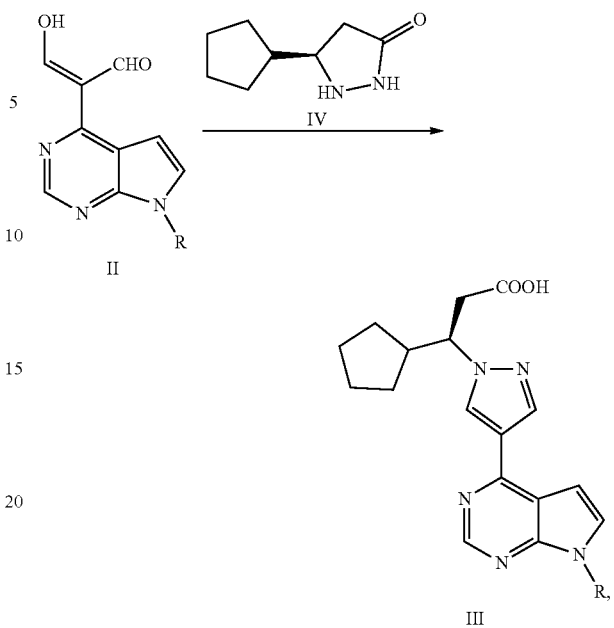

wherein, R is selected from H and an amino-protecting group.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri(C$_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

The compound of Formula IV in Step 3 of the present application may be a free base or a salt thereof.

In some embodiments of the present application, the salt of the compound of Formula IV in Step 3 may be selected from a chiral salt or an achiral salt.

In some embodiments of the present application, a chiral acid used to form the chiral salt may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, a chiral acid used to form the chiral salt may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the achiral salt is selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate, preferably hydrochloride, hydrobromide, sulfate, formate, acetate, trifluoroacetate, fumarate, maleate, methanesulfonate or p-toluene sulfonate, and more preferably hydrochloride or acetate.

In some embodiments of the present application, the molar ratio of the compound of Formula II to the compound of Formula IV or a salt thereof in Step 3 is 1.0:1.0~5.0, preferably 1.0:1.0~3.0, more preferably 1.0:1.0~1.5, and further preferably 1.0:1.0~1.2.

Step 3 of the present application may be carried out under an acidic, basic or neutral condition.

In some embodiments of the present application, the reaction in Step 3 is performed under an acidic condition.

In some embodiments of the present application, the acidic condition of Step 3 is provided by adding an acidic reagent selected from citric acid, fumaric acid, tartaric acid, maleic acid, malic acid, succinic acid, acetic acid, ascorbic acid, sulfuric acid, hydrochloric acid, hydrobromic acid, and a mixture thereof, preferably tartaric acid, acetic acid or hydrochloric acid.

In some embodiments of the present application, the reaction in Step 3 is performed under a basic condition.

In some embodiments of the present application, the basic condition of Step 3 is provided by adding an alkaline reagent selected from sodium hydroxide, potassium hydroxide, lithium hydroxide, potassium carbonate, cesium carbonate, sodium carbonate, triethylamine, diisopropylethylamine, DBU, and a mixture thereof, preferably triethylamine, sodium hydroxide or potassium hydroxide.

The solvent used in Step 3 of the present application is selected from acetic acid, ethanol, methanol, ethylene glycol monomethyl ether, ethylene glycol dimethyl ether, water, N-methylpyrrolidone, N,N-dimethylformamide, N,N-dimethylacetamide, and a mixed solvent of more than one of the above solvents, preferably water, acetic acid, ethanol, or a mixed solvent of more than one of the above three solvents.

In some embodiments of the present application, the process for preparing ruxolitinib, the compound of Formula I, according to the present application optionally further comprises Step 2: converting a compound of Formula VI into the compound of Formula II in the presence of DMF and a chlorinating agent,

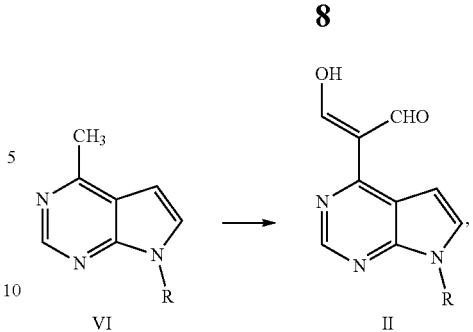

wherein, R is selected from H and an amino-protecting group.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the chlorinating agent in Step 2 is selected from oxalyl chloride, phosphorus oxychloride, thionyl chloride, and a mixture of any two or more of the above agents, preferably phosphorus oxychloride.

In some embodiments of the present application, the mole ratio of the compound of Formula VI to the chlorinating agent in Step 2 is selected from 1.0:2.0~6.0, preferably 1.0:2.0~4.0, and more preferably 1.0:2.5~3.5.

In some embodiments of the present application, the solvent used in Step 2 is selected from 1,4-dioxane, dichloromethane, tetrahydrofuran, N-methylpyrrolidone, N,N-dimethylformamide, and a mixed solvent of more than one of the above solvents, preferably N,N-dimethylformamide, 1,4-dioxane, tetrahydrofuran or a mixed solvent of more than one of the above three solvents.

In some embodiments of the present application, the process for preparing ruxolitinib, the compound of Formula I, according to the present application optionally further comprises Step 1: reacting a compound of Formula V in the presence of a catalyst and a methylating agent to obtain the compound of Formula VI, wherein, R is defined as above.

In some embodiments of the present application, the methylating agent in Step 1 is selected from methylmagnesium bromide, methylmagnesium chloride and trimethylaluminum, preferably methylmagnesium bromide.

In some embodiments of the present application, the solvent used in Step 1 is selected from toluene, dichloromethane, diethyl ether and tetrahydrofuran, preferably tetrahydrofuran or diethyl ether.

In some embodiments of the present application, the catalyst used in Step 1 is selected from Pd(PPh$_3$)$_4$, Pd(bppf)Cl$_2$ and Pd(dppf)Cl$_2$·CH$_2$Cl$_2$, preferably Pd(bppf)Cl$_2$.

In some embodiments of the present application, the molar ratio of the compound of Formula V to the catalyst and the methylating agent in Step 1 is 1:0.005~0.05:1.5~4, preferably 1:0.005~0.015:2~3.

In some embodiments of the present application, the process for preparing the compound of Formula IV or a chiral salt thereof in Step 3 comprises the following steps:

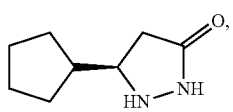

IV

Step C-1: reacting a compound of Formula X with a chiral acid in the presence of a solvent to form a chiral salt of the compound of Formula IV,

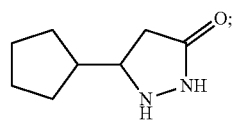

X

Step C-2: separating the chiral salt of the compound of Formula IV; and

Step C-3: optionally, treating the chiral salt of the compound of Formula IV with a base to obtain the compound of Formula IV.

In some embodiments of the present application, the chiral acid in Step C-1 may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, the chiral acid used to form the chiral salt of the compound of Formula IV in Step C-1 may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the solvent used in Step C-1 is selected from acetone, 1,4-dioxane, tetrahydrofuran, ethyl acetate, and a mixed solvent of more than one of the above solvents, preferably acetone.

In some embodiments of the present application, the molar ratio of the compound of Formula X to the chiral acid in Step C-1 is 1.0:0.2~1.0, preferably 1.0:0.3~0.7, and more preferably 1.0:0.4~0.6.

In some embodiments of the present application, the process optionally further comprises the following steps:

Step A: reacting a compound of Formula VII with malonic acid in the presence of a base to obtain a compound of Formula VIII,

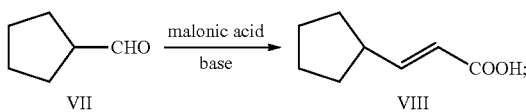

and

Step B: reacting the compound of Formula VIII with hydrazine hydrate to obtain the compound of Formula X,

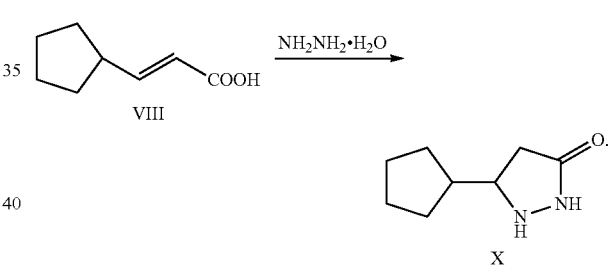

In some embodiments of the present application, the base used in Step A is selected from piperidine, triethylamine, proline, N,N-diisopropylethylamine, tetrahydropyrrole, pyridine, and 4-dimethylaminopyridine, preferably piperidine.

In some embodiments of the present application, the solvent used in Step A is selected from pyridine, acetonitrile, ethanol, N,N-dimethylformamide, dimethyl sulfoxide, ethyl acetate, acetone, and 1,4-dioxane, preferably pyridine.

In some embodiments of the present application, the solvent used in Step B is selected from hydrazine hydrate, 1,4-dioxane, ethanol, methanol, isopropanol, tetrahydrofuran, N-methylpyrrolidone, N,N-dimethylformamide, and a mixed solvent of more than one of the above solvents, preferably hydrazine hydrate.

In another aspect, the present application provides a process for preparing ruxolitinib, the compound of Formula I, comprising the following steps:

Step 2: converting a compound of Formula VI into a compound of Formula II in the presence of DMF and a chlorinating agent,

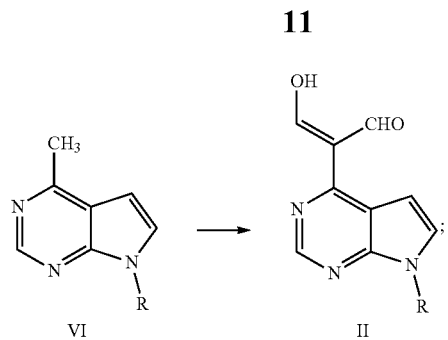

Step 3: reacting the compound of Formula II with a compound of Formula IV or a salt thereof to obtain a compound of Formula III,

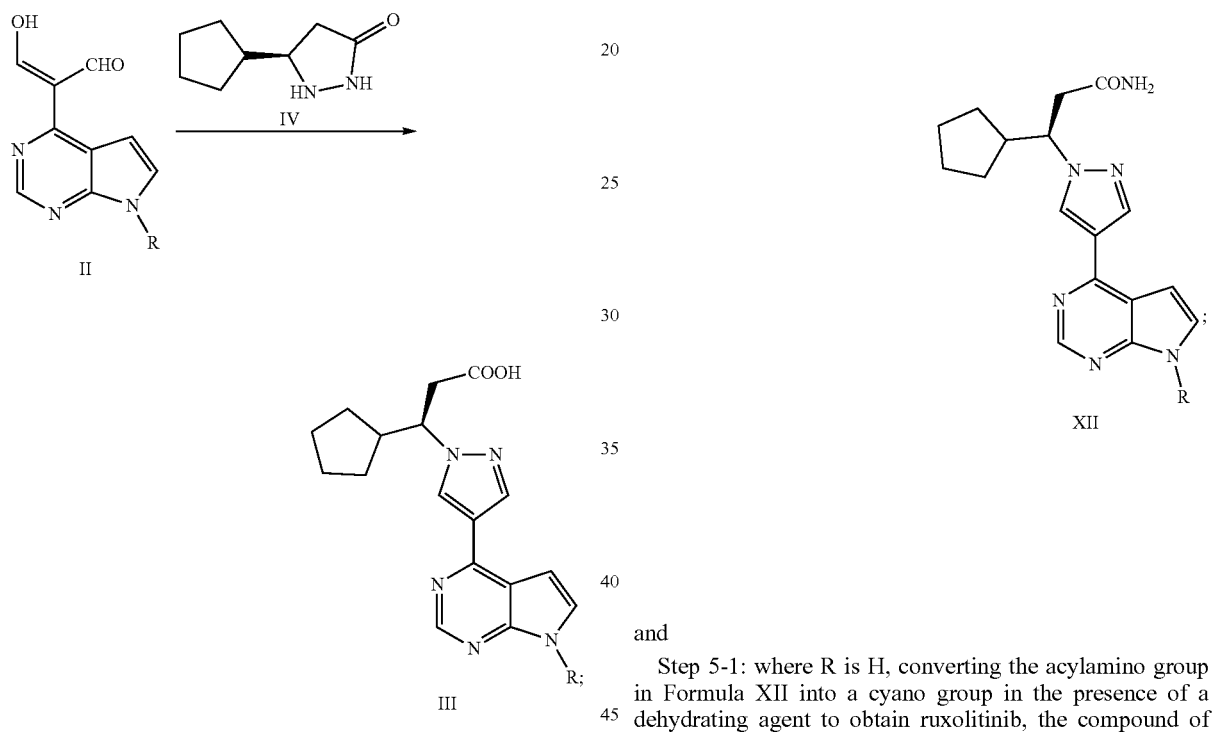

Step 4: converting the compound of Formula III into a compound of Formula XI, and then converting the compound of Formula XI into a compound of Formula XII in the presence of an aminating agent, and Step 5-1: where R is H, converting the acylamino group in Formula XII into a cyano group in the presence of a dehydrating agent to obtain ruxolitinib, the compound of Formula I, or Step 5-2: where R is an amino-protecting group, converting the acylamino group in Formula XII into a cyano group and removing the amino-protecting group R to obtain ruxolitinib, the compound of Formula I,

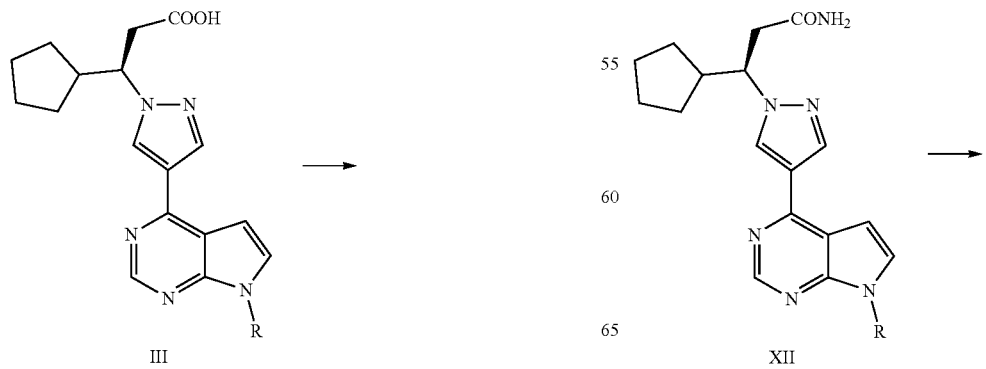

-continued

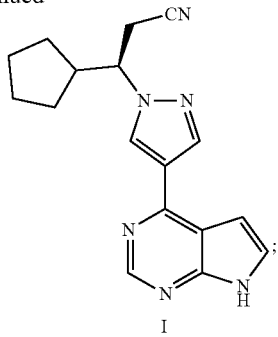

wherein R is selected from H and an amino-protecting group, and X is selected from Cl and Br.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the chlorinating agent in Step 2 is selected from oxalyl chloride, phosphorus oxychloride, thionyl chloride, and a mixture of any two or more of the above agents, preferably phosphorus oxychloride.

In some embodiments of the present application, the mole ratio of the compound of Formula VI to the chlorinating agent in Step 2 is selected from 1.0:2.0~6.0, preferably 1.0:2.0~4.0, and more preferably 1.0:2.5~3.5.

In some embodiments of the present application, the solvent used in Step 2 is selected from 1,4-dioxane, dichloromethane, tetrahydrofuran, N-methylpyrrolidone, N,N-dimethylformamide, and a mixed solvent of more than one of the above solvents, preferably N,N-dimethylformamide, 1,4-dioxane, tetrahydrofuran or a mixed solvent of more than one of the above three solvents.

In some embodiments of the present application, the salt of the compound of Formula IV in Step 3 may be selected from a chiral salt or an achiral salt.

In some embodiments of the present application, a chiral acid used to form the chiral salt in Step 3 may be selected from the following acids or an enantiomeric excess form thereof: mandelic acid, 2-chloromandelic acid, camphoric acid, lactic acid, malic acid, 3-bromo camphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, a chiral acid used to form the chiral salt in Step 3 may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the achiral salt in Step 3 is selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate, preferably hydrochloride, hydrobromide, sulfate, formate, acetate, trifluoroacetate, fumarate, maleate, methanesulfonate or p-toluene sulfonate, and more preferably hydrochloride or acetate.

In some embodiments of the present application, the molar ratio of the compound of Formula II to the compound of Formula IV in Step 3 is 1.0:1.0~5.0, preferably 1.0:1.0~3.0, more preferably 1.0:1.0~1.5, and further preferably 1.0:1.0~1.2.

The reaction of the compound of Formula II with the compound of Formula IV or a salt thereof to obtain the compound of Formula III (i.e., the reaction in Step 3) may be performed under a acidic, basic or neutral condition.

In some embodiments of the present application, the reaction in Step 3 is performed under an acidic condition.

In some embodiments of the present application, the acidic condition in Step 3 is provided by adding an acidic reagent selected from citric acid, fumaric acid, tartaric acid, maleic acid, malic acid, succinic acid, acetic acid, ascorbic acid, sulfuric acid, hydrochloric acid, hydrobromic acid, and a mixture thereof, preferably tartaric acid, acetic acid or hydrochloric acid.

In some embodiments of the present application, the reaction in Step 3 is performed under a basic condition.

In some embodiments of the present application, the basic condition in Step 3 is provided by adding an alkaline reagent selected from sodium hydroxide, potassium hydroxide, lithium hydroxide, potassium carbonate, cesium carbonate, sodium carbonate, potassium bicarbonate, sodium bicarbonate, triethylamine, diisopropylethylamine, DBU, and a mixture thereof, preferably triethylamine, sodium hydroxide or potassium hydroxide.

In some embodiments of the present application, the solvent used in Step 3 is selected from acetic acid, ethanol, methanol, ethylene glycol monomethyl ether, ethylene glycol dimethyl ether, water, N-methylpyrrolidone, N,N-dimethylformamide, N,N-dimethylacetamide, and a mixed solvent of more than one of the above solvents, preferably water, acetic acid, ethanol, or a mixed solvent of more than one of the above three solvents.

In some embodiments of the present application, the reagent used in the reaction of converting the compound of Formula III into the compound of Formula XI in Step 4 is selected from one or more of phosphorus trichloride, phosphorus pentachloride, thionyl chloride, and oxalyl chloride, preferably oxalyl chloride.

In some embodiments of the present application, the solvent used in the reaction of converting the compound of Formula III into the compound of Formula XI in Step 4 is selected from tetrahydrofuran, dichloromethane, trichloromethane, chlorobenzene, acetonitrile, DMA, NMP, ethyl acetate, isopropyl acetate, toluene, xylene, and a mixed solvent of more than one of the above solvents, preferably NMP, dichloromethane, or a mixed solvent thereof.

In some embodiments of the present application, the aminating agent used in the reaction of converting the compound of Formula XI into the compound of Formula XII in Step 4 is selected from one or more of aqueous ammonia, liquid ammonia, and ammonia gas, preferably aqueous ammonia.

In some embodiments of the present application, the solvent used in the reaction of converting the compound of Formula XI into the compound of Formula XII in Step 4 is selected from tetrahydrofuran, dichloromethane, trichloromethane, chlorobenzene, acetonitrile, DMA, NMP, ethyl acetate, isopropyl acetate, toluene, xylene, and a mixed solvent of more than one of the above solvents, preferably dichloromethane, tetrahydrofuran, or a mixed solvent thereof.

In some embodiments of the present application, the dehydrating agent used in Step 5-1 is selected from one or more of phosphorus oxychloride, cyanuric chloride, phosphorus pentoxide, thionyl chloride, trifluoroacetic anhydride, trifluoro sulfonic anhydride, and oxalyl chloride, preferably phosphorus oxychloride or cyanuric chloride.

In some embodiments of the present application, the solvent used in Step 5-1 is selected from tetrahydrofuran, dichloromethane, trichloromethane, chlorobenzene, acetonitrile, DMA, NMP, DMSO, ethyl acetate, isopropyl acetate, toluene, xylene, and a mixed solvent of more than one of the above solvents, preferably dichloromethane, NMP, or a mixed solvent thereof.

In some embodiments of the present application, the molar ratio of the compound of Formula XII (R═H) to the dehydrating agent in Step 5-1 is 1:1~10, preferably 1:3~8, more preferably 1:4~7, and further preferably 1:5~7.

In the present application, in order to implement the process according to the present application, a person skilled in the art may change the order of the steps in Step 5-2 on the basis of the existing embodiments. For example, when preparing ruxolitinib from the compound of Formula XII (R=amino-protecting group), the reaction of converting the acylamino group into a cyano group may be performed firstly and then the reaction of removing the protecting group R is performed, or the reaction of removing the protecting group R may be performed firstly and then the reaction of converting the acylamino group into a cyano group is performed, both of which are within the protection scope of the present application.

In some embodiments of the present application, the dehydrating agent used in the reaction of converting the acylamino group into a cyano group in Step 5-2 is selected from one or more of phosphorus oxychloride, cyanuric chloride, phosphorus pentoxide, thionyl chloride, trifluoroacetic anhydride, trifluoro sulfonic anhydride, and oxalyl chloride, preferably phosphorus oxychloride or cyanuric chloride.

In some embodiments of the present application, the solvent used in the reaction of converting the acylamino group into a cyano group in Step 5-2 is selected from tetrahydrofuran, dichloromethane, trichloromethane, chlorobenzene, acetonitrile, DMA, NMP, DMSO, ethyl acetate, isopropyl acetate, toluene and xylene, preferably dichloromethane or NMP.

In some embodiments of the present application, the molar ratio of the compound of Formula XII (R=amino-protecting group) to the dehydrating agent in the reaction of converting the acylamino group into a cyano group in Step 5-2 is 1:1~10, preferably 1:3~8, more preferably 1:4~7, and further preferably 1:5~7.

In some embodiments of the present application, the reaction of removing the protecting group R in Step 5-2 may be performed under an acidic or basic condition. Under an acidic or basic condition, the reaction of removing the protecting group R may be performed by selecting an appropriate catalyst and solvent, respectively.

In some embodiments of the present application, the catalyst used in the reaction of removing the amino-protecting group R in Step 5-2 is selected from trifluoroacetic acid, trifluoroacetic anhydride, lithium tetrafluoroborate and boron trifluoride-diethyl etherate, preferably trifluoroacetic acid or boron trifluoride-diethyl etherate.

In some embodiments of the present application, the solvent used in the reaction of removing the amino-protecting group R in Step 5-2 is selected from dichloromethane, tetrahydrofuran, acetonitrile, water, NMP, DMA and DMF, preferably acetonitrile or NMP.

In some embodiments of the present application, the catalyst used in the reaction of removing the amino-protecting group R in Step 5-2 is selected from sodium carbonate, cesium carbonate, potassium carbonate, sodium hydroxide, potassium hydroxide, lithium hydroxide, potassium tert-butoxide, sodium tert-butoxide, hydrazine hydrate and tetrabutylammonium fluoride, preferably lithium hydroxide or potassium carbonate.

In some embodiments of the present application, the solvent used in the reaction of removing the protecting group R in Step 5-2 is selected from ethanol, water, methanol, tetrahydrofuran and isopropanol, preferably water or tetrahydrofuran.

In some embodiments of the present application, the process for preparing ruxolitinib, the compound of Formula I, according to the present application optionally further comprises the following Step 1: reacting a compound of Formula V in the presence of a catalyst and a methylating agent to obtain the compound of Formula VI:

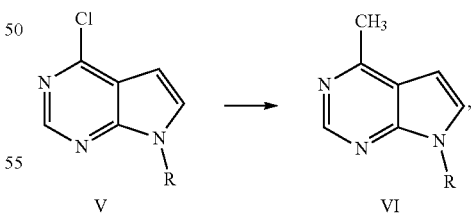

wherein, R is defined as above.

In some embodiments of the present application, the methylating agent in Step 1 is selected from methylmagnesium bromide, methylmagnesium chloride and trimethylaluminum, preferably methylmagnesium bromide.

In some embodiments of the present application, the solvent used in Step 1 is selected from toluene, dichloromethane, diethyl ether and tetrahydrofuran, preferably tetrahydrofuran or diethyl ether.

In some embodiments of the present application, the catalyst used in Step 1 is selected from Pd(PPh$_3$)$_4$, Pd(bppf)Cl$_2$ and Pd(dppf)Cl$_2$.CH$_2$Cl$_2$, preferably Pd(bppf)Cl$_2$.

In some embodiments of the present application, the molar ratio of the compound of Formula V to the catalyst and the methylating agent in Step 1 is 1:0.005~0.05:1.5~4, preferably 1:0.005~0.015:2~3.

In a further aspect, the present application provides a compound of Formula II-1, a compound of Formula II-2, a compound of Formula IV, D-tartrate salt of the compound of Formula IV, a compound of Formula III-1, a compound of Formula XI-1, a compound of Formula XI-2 and a compound of Formula XII-1.

II-1

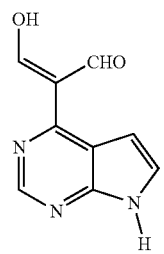

II-2

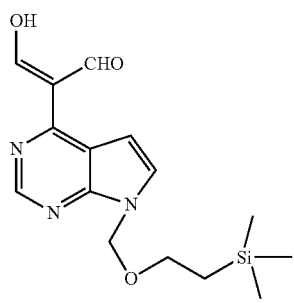

IV

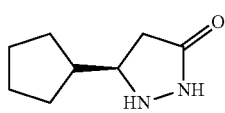

III-1

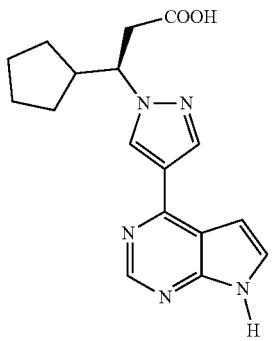

XI-1

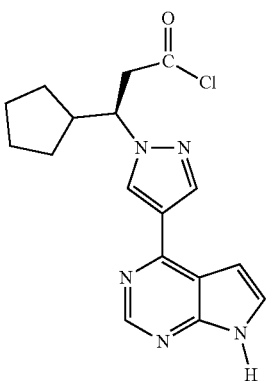

XI-2

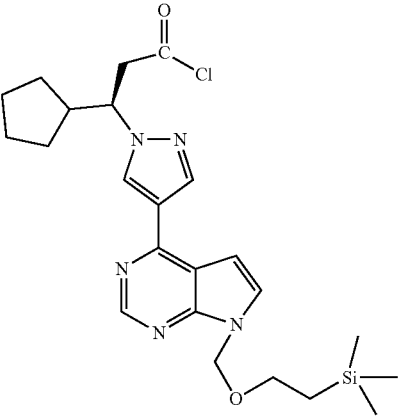

XII-1

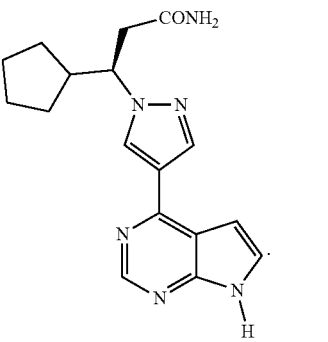

In still another aspect, the present application provides use of the compound of Formula II-1, the compound of Formula II-2, the compound of Formula IV, the D-tartrate salt of the compound of Formula IV, the compound of Formula III-1, the compound of Formula XI-1, the compound of Formula XI-2 and/or the compound of Formula XII-1 in the preparation of ruxolitinib.

In some embodiments of the present application, the use of the compound of Formula IV or the D-tartaric acid salt thereof in the preparation of ruxolitinib comprises utilizing the compound of Formula IV or the D-tartaric acid salt thereof to form the pyrazole ring structure in ruxolitinib.

In some embodiments of the present application, the use of the compound of Formula IV or the D-tartaric acid salt thereof in the preparation of ruxolitinib comprises utilizing the compound of Formula IV to introduce the chiral carbon atom of ruxolitinib.

In another aspect, the present application provides a process for preparing a compound of Formula III, comprising reacting a compound of Formula II with the compound of Formula IV or a salt thereof to obtain a compound of Formula III,

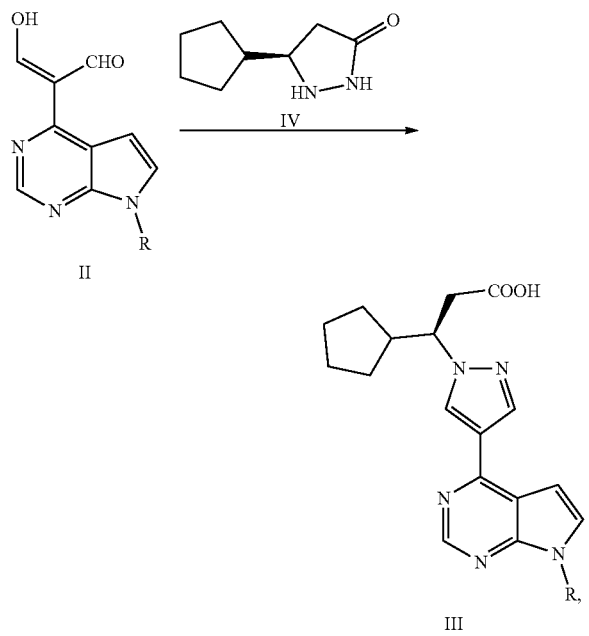

wherein R is selected from H and an amino-protecting group.

In some embodiments of the present application, the amino-protecting group is not removed from the compound in the corresponding reaction step.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the salt of the compound of Formula IV may be selected from a chiral salt or an achiral salt.

In some embodiments of the present application, a chiral acid used to form the chiral salt may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, a chiral acid used to form the chiral salt may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the achiral salt is selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate, preferably is selected from hydrochloride, hydrobromide, sulfate, formate, acetate, trifluoroacetate, fumarate, maleate, methanesulfonate and p-toluene sulfonate, and more preferably is selected from hydrochloride and acetate.

In some embodiments of the present application, the molar ratio of the compound of Formula II to the compound of Formula IV is 1.0:1.0~5.0, preferably 1.0:1.0~3.0, more preferably 1.0:1.0~1.5, and further preferably 1.0:1.0~1.2.

The reaction of the compound of Formula II with the compound of Formula IV or a salt thereof to obtain the compound of Formula III according to the present application may be performed under an acidic, basic or neutral condition.

In some embodiments of the present application, the reaction is performed under an acidic condition.

In some embodiments of the present application, the acidic condition is provided by adding an acidic reagent selected from citric acid, fumaric acid, tartaric acid, maleic acid, malic acid, succinic acid, acetic acid, ascorbic acid, sulfuric acid, hydrochloric acid, hydrobromic acid, and a mixture thereof, preferably tartaric acid, acetic acid or hydrochloric acid.

In some embodiments of the present application, the reaction is performed under a basic condition.

In some embodiments of the present application, the basic condition is provided by adding an alkaline reagent selected from sodium hydroxide, potassium hydroxide, lithium hydroxide, potassium carbonate, cesium carbonate, sodium carbonate, potassium bicarbonate, sodium bicarbonate, triethylamine, diisopropylethylamine, DBU, and a mixture thereof, preferably triethylamine, sodium hydroxide or potassium hydroxide.

In some embodiments of the present application, the solvent used therein is selected from acetic acid, ethanol, methanol, ethylene glycol monomethyl ether, ethylene glycol dimethyl ether, water, N-methylpyrrolidone, N,N-dimethylformamide, N,N-dimethylacetamide, or a mixed solvent of more than one of the above solvents, preferably water, acetic acid, ethanol, or a mixed solvent of more than one of the above three solvents.

In another aspect, the present application provides a process for preparing a compound of Formula XII, comprising reacting a compound of Formula II with a compound of Formula IV or a salt thereof in the presence of $NH_3$ to obtain a compound of Formula XII,

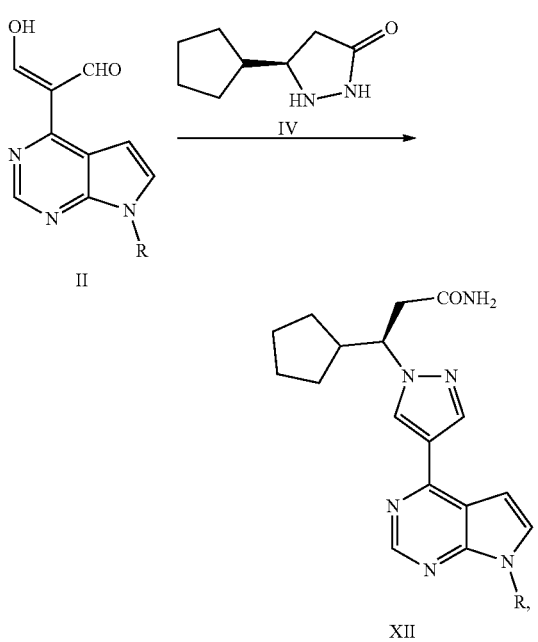

wherein R is selected from H and an amino-protecting group.

In some embodiments of the present application, the amino-protecting group is not removed from the compound in the corresponding reaction step.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the salt of the compound of Formula IV may be selected from a chiral salt or an achiral salt.

In some embodiments of the present application, a chiral acid used to form the chiral salt may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, a chiral acid used to form the chiral salt may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the achiral salt is selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate, preferably hydrochloride, hydrobromide, sulfate, formate, acetate, trifluoroacetate, fumarate, maleate, methanesulfonate or p-toluene sulfonate, and more preferably hydrochloride or acetate.

In some embodiments of the present application, the reagent providing $NH_3$ is selected from one or more of aqueous ammonia, aminomethanol, ammonia gas, and liquid ammonia, preferably aqueous ammonia.

In some embodiments of the present application, the solvent used in the reaction of the compound of Formula II with the compound of Formula IV or a salt thereof to obtain the compound of Formula XII is selected from tetrahydrofuran, dichloromethane, trichloromethane, chlorobenzene, acetonitrile, DMA, NMP, ethyl acetate, isopropyl acetate, toluene, xylene and a mixed solvent of more than one of the above solvents, preferably tetrahydrofuran.

In another aspect, the present application provides a process for preparing ruxolitinib, the compound of Formula I, comprising the following steps:

Step (1): reacting a compound of Formula II with a compound of Formula IV or a salt thereof in the presence of $NH_3$ to obtain a compound of Formula XII,

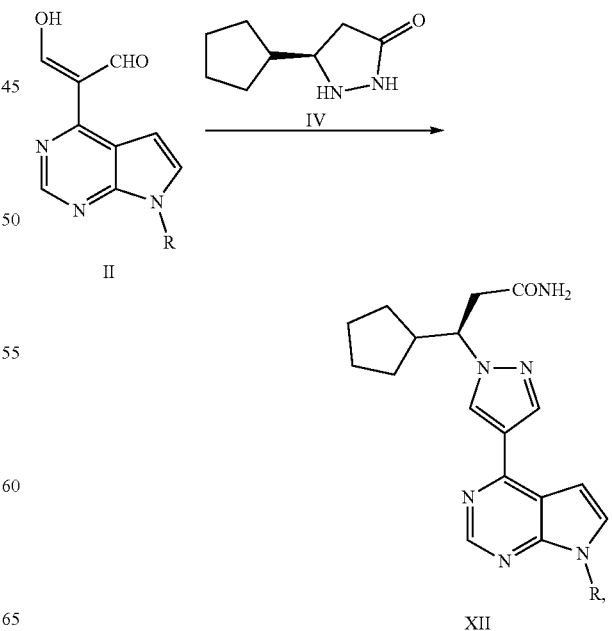

wherein, R is selected from H and an amino-protecting group; and

Step (2-1): where R is H, converting the acylamino group in Formula XII into a cyano group in the presence of a dehydrating agent to obtain ruxolitinib, the compound of Formula I, or Step (2-2): where R is an amino-protecting group, converting the acylamino group in Formula XII into a cyano group and removing the amino-protecting group R to obtain ruxolitinib, the compound of Formula I;

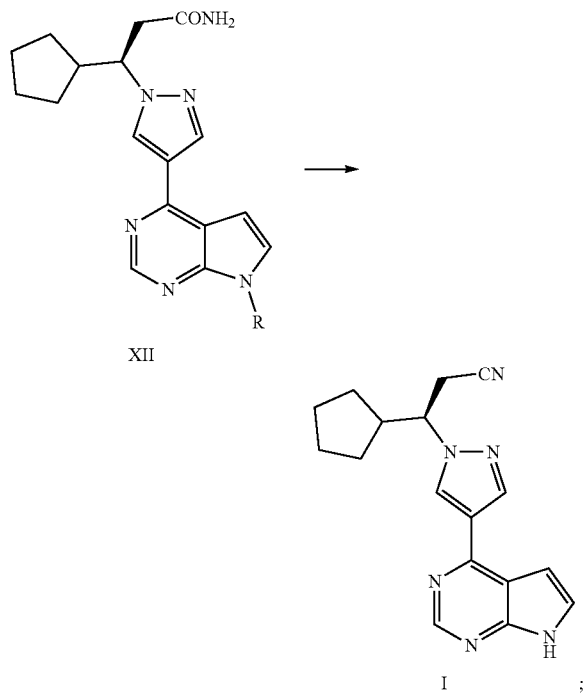

wherein, R is selected from H and an amino-protecting group.

In some embodiments of the present application, the amino-protecting group in Step (1) is not removed from the compound in the corresponding reaction step.

In some embodiments of the present application, the amino-protecting group in Step (1) and Step (2-2) is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the salt of the compound of Formula IV in Step (1) may be selected from a chiral salt or an achiral salt.

In some embodiments of the present application, a chiral acid used to form the chiral salt may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, a chiral acid used to form the chiral salt may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the achiral salt is selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate, preferably hydrochloride, hydrobromide, sulfate, formate, acetate, trifluoroacetate, fumarate, maleate, methanesulfonate or p-toluene sulfonate, and more preferably hydrochloride or acetate.

In some embodiments of the present application, the reagent providing $NH_3$ in Step (1) is selected from one or more of aqueous ammonia, aminomethanol, ammonia gas, and liquid ammonia, preferably aqueous ammonia.

In some embodiments of the present application, the solvent used in Step (1) is selected from tetrahydrofuran, dichloromethane, trichloromethane, chlorobenzene, acetonitrile, DMA, NMP, ethyl acetate, isopropyl acetate, toluene, xylene and a mixed solvent of more than one of the above solvents, preferably tetrahydrofuran.

In some embodiments of the present application, the dehydrating agent used in Step (2-1) is selected from one or more of phosphorus oxychloride, cyanuric chloride, phosphorus pentoxide, thionyl chloride, trifluoroacetic anhydride, trifluoro sulfonic anhydride, and oxalyl chloride, preferably phosphorus oxychloride or cyanuric chloride.

In some embodiments of the present application, the solvent used in Step (2-1) is selected from tetrahydrofuran, dichloromethane, trichloromethane, chlorobenzene, acetonitrile, DMA, NMP, DMSO, ethyl acetate, isopropyl acetate, toluene, xylene, and a mixed solvent of more than one of the above solvents, preferably dichloromethane, NMP, or a mixed solvent thereof.

In some embodiments of the present application, the molar ratio of the compound of Formula XII (R=H) to the dehydrating agent in Step (2-1) is 1:1~10, preferably 1:3~8, more preferably 1:4~7, and further preferably 1:5~7.

In the present application, in order to implement the process according to the present application, a person skilled in the art may change the order of the steps in Step (2-2) on the basis of the existing embodiments. For example, when preparing ruxolitinib from the compound of Formula XII (R=amino-protecting group), the reaction of converting the acylamino group into a cyano group may be performed firstly and then the reaction of removing the protecting group R is performed, or the reaction of removing the protecting group R may be performed firstly and then the reaction of converting the acylamino group into a cyano group is performed, both of which are within the protection scope of the present application.

In some embodiments of the present application, the dehydrating agent used in the reaction of converting the acylamino group into a cyano group in Step (2-2) is selected from one or more of phosphorus oxychloride, cyanuric chloride, phosphorus pentoxide, thionyl chloride, trifluoroacetic anhydride, trifluoro sulfonic anhydride, and oxalyl chloride, preferably phosphorus oxychloride or cyanuric chloride.

In some embodiments of the present application, the solvent used in the reaction of converting the acylamino group into a cyano group in Step (2-2) is selected from tetrahydrofuran, dichloromethane, trichloromethane, chlorobenzene, acetonitrile, DMA, NMP, DMSO, ethyl acetate, isopropyl acetate, toluene and xylene, preferably dichloromethane or NMP.

In some embodiments of the present application, the molar ratio of the compound of Formula XII (R=amino-protecting group) to the dehydrating agent in the reaction of converting the acylamino group into a cyano group in Step (2-2) is 1:1~10, preferably 1:3~8, more preferably 1:4~7, and further preferably 1:5~7.

In some embodiments of the present application, the reaction of removing the protecting group R in Step (2-2) may be performed under an acidic or basic condition. Under an acidic or basic condition, the reaction of removing the protecting group R may be performed by selecting an appropriate catalyst and solvent.

In some embodiments of the present application, the catalyst used in the reaction of removing the amino-protecting group R in Step (2-2) is selected from trifluoroacetic acid, trifluoroacetic anhydride, lithium tetrafluoroborate and boron trifluoride-diethyl etherate, preferably trifluoroacetic acid or boron trifluoride-diethyl etherate.

In some embodiments of the present application, the solvent used in the reaction of removing the amino-protecting group R in Step (2-2) is selected from dichloromethane, tetrahydrofuran, acetonitrile, water, NMP, DMA and DMF, preferably acetonitrile or NMP.

In some embodiments of the present application, the catalyst used in the reaction of removing the amino-protecting group R in Step (2-2) is selected from sodium carbonate, cesium carbonate, potassium carbonate, sodium hydroxide, potassium hydroxide, lithium hydroxide, potassium tert-butoxide, sodium tert-butoxide, hydrazine hydrate and tetrabutylammonium fluoride, preferably lithium hydroxide or potassium carbonate.

In some embodiments of the present application, the solvent used in the reaction of removing the protecting group R in Step (2-2) is selected from ethanol, water, methanol, tetrahydrofuran and isopropanol, preferably water or tetrahydrofuran.

In another aspect, the present application provides a process for preparing a compound of Formula II, comprising the following steps: converting a compound of Formula VI into the compound of Formula II in the presence of DMF and a chlorinating agent,

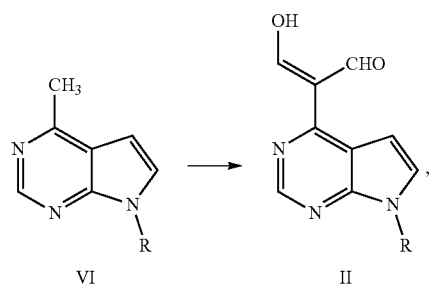

wherein, R is selected from H and an amino-protecting group.

In some embodiments of the present application, the amino-protecting group is selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM), preferably 2-(trimethylsilyl)ethoxymethyl (SEM), N-pivaloyloxymethyl (POM), p-nitrophenylsulfonyl, p-toluenesulfonyl, phenylsulfonyl, methanesulfonyl or benzyl, and more preferably 2-(trimethylsilyl)ethoxymethyl (SEM).

In some embodiments of the present application, the chlorinating agent is selected from oxalyl chloride, phosphorus oxychloride, thionyl chloride, and a mixture of any two or more of the above agents, preferably phosphorus oxychloride.

In some embodiments of the present application, the mole ratio of the compound of Formula VI to the chlorinating agent is selected from 1.0:2.0~6.0, preferably 1.0:2.0~4.0, and more preferably 1.0:2.5~3.5.

In some embodiments of the present application, the solvent used therein is selected from 1,4-dioxane, dichloromethane, tetrahydrofuran, N-methylpyrrolidone, N,N-dimethylformamide, and a mixed solvent of more than one of the above solvents, preferably N,N-dimethylformamide, 1,4-dioxane, tetrahydrofuran or a mixed solvent of more than one of the above three solvents.

In some embodiments of the present application, the process for preparing the compound of Formula II according to the present application optionally further comprises: reacting a compound of Formula V in the presence of a catalyst and a methylating agent to obtain a compound of Formula VI,

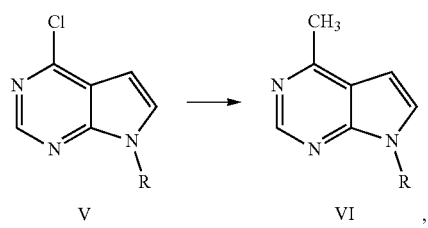

wherein, R is defined as above.

In some embodiments of the present application, the methylating agent is selected from methylmagnesium bromide, methylmagnesium chloride and trimethylaluminum, preferably methylmagnesium bromide.

In some embodiments of the present application, the solvent used therein is selected from toluene, dichloromethane, diethyl ether and tetrahydrofuran, preferably tetrahydrofuran or diethyl ether.

In some embodiments of the present application, the catalyst used therein is selected from Pd(PPh₃)₄, Pd(bppf)Cl₂ and Pd(dppf)Cl₂·CH₂Cl₂, preferably Pd(bppf)Cl₂.

In some embodiments of the present application, the molar ratio of the compound of Formula V to the catalyst and the methylating agent is 1:0.005~0.05:1.5~4, preferably 1:0.005~0.015:2~3.

In a further aspect, the present application provides a process for preparing the compound of Formula IV or a chiral salt thereof, comprising the following steps:

Step C-1: reacting a compound of Formula X with a chiral acid in the presence of a solvent to form a chiral salt of the compound of Formula IV,

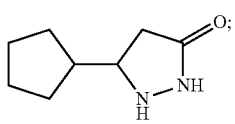

Step C-2: separating the chiral salt of the compound of Formula IV; and

Step C-3: optionally, treating the chiral salt of the compound of Formula IV with a base to obtain the compound of Formula IV.

In some embodiments of the present application, the chiral acid in Step C-1 may be selected from the following acids or an enantiomeric excess form thereof: mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethylbicyclo[2,2,1]heptan-1-methylene sulfonic acid, 2-acrylamide-7,7-dimethylbicyclo[2,2,1]heptan-1-methylene sulfonic acid, or tartaric acid and acyl derivatives thereof, preferably lactic acid, malic acid, camphoric acid, 10-camphorsulfonic acid, tartaric acid, diacetyl tartaric acid, dibenzoyl tartaric acid, di-p-toluoyl tartaric acid, di-p-anisoyl tartaric acid, di-p-chlorobenzoyl tartaric acid, di-p-bromobenzoyl tartaric acid, di-p-fluorobenzoyl tartaric acid, di-p-nitrobenzoyl tartaric acid, di-p-aminobenzoyl tartaric acid or di-p-cyanobenzoyl tartaric acid, and more preferably tartaric acid, diacetyl tartaric acid, dibenzoyl tartaric acid or di-p-toluoyl tartaric acid.

In some embodiments of the present application, the chiral acid used to form the chiral salt of the compound of Formula IV in Step C-1 may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

In some embodiments of the present application, the solvent used in Step C-1 is selected from acetone, 1,4-dioxane, tetrahydrofuran, ethyl acetate, and a mixed solvent of more than one of the above solvents, preferably acetone.

In some embodiments of the present application, the molar ratio of the compound of Formula X to the chiral acid in Step C-1 is 1.0:0.2~1.0, preferably 1.0:0.3~0.7, and more preferably 1.0:0.4~0.6.

In some embodiments of the present application, the process for preparing the compound of Formula IV or a chiral salt thereof optionally further comprises the following steps:

Step A: reacting a compound of Formula VII with malonic acid in the presence of a base to obtain a compound of Formula VIII,

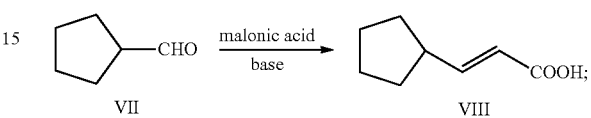

and

Step B: reacting the compound of Formula VIII with hydrazine hydrate to obtain the compound of Formula X,

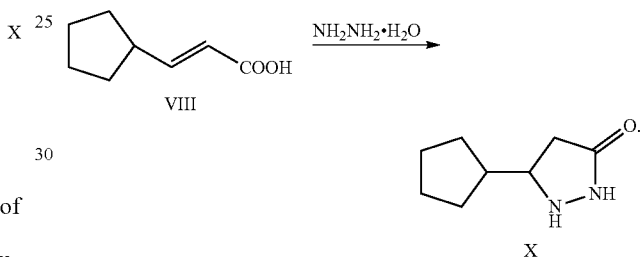

In some embodiments of the present application, the base used in Step A is selected from piperidine, triethylamine, proline, N,N-diisopropylethylamine, tetrahydropyrrole, pyridine, and 4-dimethylaminopyridine, preferably piperidine.

In some embodiments of the present application, the solvent used in Step A is selected from pyridine, acetonitrile, ethanol, N,N-dimethylformamide, dimethyl sulfoxide, ethyl acetate, acetone, and 1,4-dioxane, preferably pyridine.

In some embodiments of the present application, the solvent used in Step B is selected from hydrazine hydrate, 1,4-dioxane, ethanol, methanol, isopropanol, tetrahydrofuran, N-methylpyrrolidone, N,N-dimethylformamide, and a mixed solvent of more than one of the above solvents, preferably hydrazine hydrate.

Definitions

The amino-protecting group described herein includes, but not limited to, those listed in "Protective Groups in Organic Synthesis" (4th Edition, John Wiley & Sons: New Jersey), which is incorporated herein by reference. In the present application, those skilled in the art can use known methods to attach an amino-protecting group to or remove it from the reaction compound in accordance with the characteristics of the amino-protecting group.

The amino-protecting group described herein may be selected from benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl) ethoxycarbonyl (Tsc), tert-butoxycarbonyl (Boc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-phenylsulfonylethyl, p-nitrophenylsulfonyl, p-toluenesulfonyl, phenylsulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl (Bum), benzyloxymethyl (Bom), 2-tetrahydropyranyl (THP), tri($C_{1-4}$alkyl)silyl, 1,1-diethoxymethyl, 2-(trimethylsilyl)ethoxymethyl (SEM) and N-pivaloyloxymethyl (POM).

In the present application, according to the structural characteristics of the compound of Formula II, those skilled in the art can predict that it has a keto-enol tautomerism property (Fundamentals of Organic Chemistry, 3rd Edition, Higher Education Press, ISBN 7-04-016637-2, pages 654-656), and the keto-enol tautomers of the compound of Formula II are also within the protection scope of the present application. The keto-enol tautomers of the compound of Formula II described herein include the following structures:

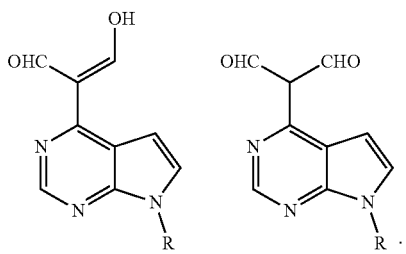

In the present application, the amino-protecting group refers to a functional group that reversibly converts an amino group into an inert group except for a specific functional group where a desired reaction occurs during the process of a reaction. In the reaction of each step described in the present application, the amino-protecting group is not essential, and those skilled in the art may optionally introduce or not introduce an amino-protecting group into the reaction substrate according to the reaction conditions of each step and the requirements for the reaction result. For example, in the following reaction step,

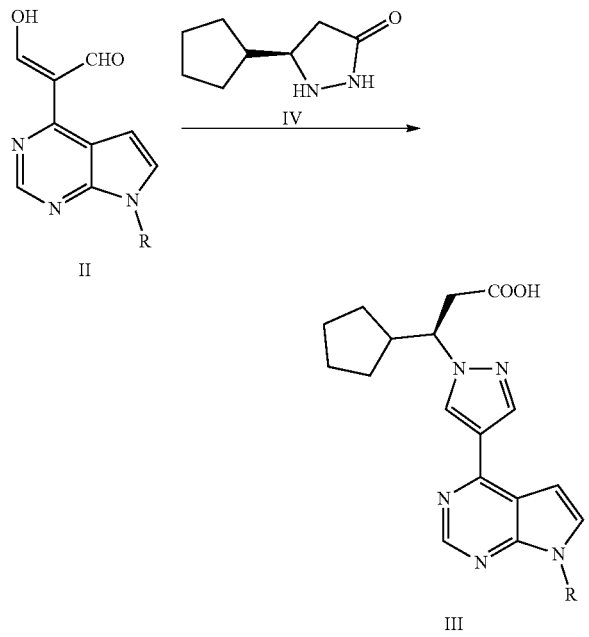

R is selected from the group consisting of H and an amino-protecting group,

An experimenter finds that the reaction conditions are mild; the reaction may be carried out under an acidic, basic, or neutral condition; there is no strong oxidation, strong reduction or active catalytic environment in the reaction system; and where R is selected from either H or an amino-protecting group, the synthetic scheme described in the present application can be achieved.

The compound of Formula IV described in the present application may be used in its free base form or its salt form. The salt form may be selected from a chiral salt or an achiral salt. The chiral salt refers to a salt formed from an acidic compound having an asymmetric atom (eg, a carbon atom) and an enantiomeric excess of the corresponding chiral base compound. The chiral acid refers to an acid having an asymmetric atom, including enantiomeric excess form or enantiomeric non-excessive form thereof. The chiral salt may be selected from mandelate, 2-chloromandelate, camphorate, lactate, malate, 3-bromocamphor-8-sulfonate, 3-bromocamphor-10-sulfonate, 10-camphorsulfonate, 2-amino-7,7-dimethylbicyclo[2,2,1]heptan-1-methylenesulfonate, 2-acrylamide-7,7-dimethylbicyclo[2,2,1]heptan-1-methylenesulfonate and a salt of tartaric acid or an acyl derivative thereof; preferably is selected from lactate, malate, camphorate, 10-camphorsulfonate, tartrate, diacetyl tartrate, dibenzoyl tartrate, di-p-toluoyl tartrate, di-p-anisoyl tartrate, di-p-chlorobenzoyl tartrate, di-p-bromobenzoyl tartrate, di-p-fluorobenzoyl tartrate, di-p-nitrobenzoyl tartrate, di-p-aminobenzoyl tartrate and di-p-cyanobenzoyl tartrate.

The chiral salt described in the present application may be selected from enantiomeric excess form thereof. For example, the enantiomeric excess form of a salt of tartaric acid or an acyl derivative thereof may be selected from D-tartaric acid, D-diacetyl tartaric acid, D-dibenzoyl tartaric acid, D-di-p-toluoyl tartaric acid, D-di-p-anisoyl tartaric acid, D-di-p-chlorobenzoyl tartaric acid, D-di-p-bromobenzoyl tartaric acid, D-di-p-fluorobenzoyl tartaric acid, D-di-p-nitrobenzoyl tartaric acid, D-di-p-aminobenzoyl tartaric acid and D-di-p-cyanobenzoyl tartaric acid.

Tartaric acid and an acyl derivative thereof described in the present application also include a hydrate form thereof. For example, tartaric acid includes tartaric acid and tartaric acid monohydrate, and D-dibenzoyltartaric acid includes D-dibenzoyltartaric acid and D-dibenzoyltartaric acid monohydrate.

The achiral salt described in the present application may be selected from hydrochloride, hydrobromide, nitrate, sulfate, phosphate, formate, acetate, trifluoroacetate, fumarate, oxalate, maleate, citrate, succinate, methanesulfonate, benzenesulfonate and p-toluene sulfonate.

The molar ratio and the mole ratio described in the present application are equivalent to each other.

In the present application, the compound represented by Formula V in which R is H may be commercially available, and the compound represented by Formula V in which R is an amino-protecting group may be prepared by a known method using the compound represented by Formula V in which R is H as a starting material according to the characteristics of different amino-protecting groups. For example, when the compound represented by Formula V has a structure of the following Formula V-2,

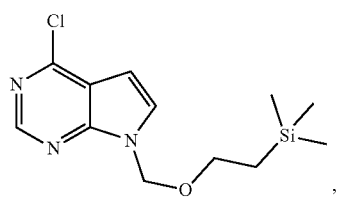

V-2

The compound of Formula V-2 can be obtained by using 4-chloropyrrolo[2,3-d]pyrimidine as a starting material and reacting it with 2-(trimethylsilyl)ethoxymethyl chloride under a basic condition.

In the present application, the compound of Formula VII may be commercially available.

In the present application, the term "DMF" refers to N,N-dimethylformamide.

In the present application, the term "NMP" refers to N-methylpyrrolidone.

In the present application, the term "SEM-" refers to 2-(trimethylsilyl)ethoxymethyl.

In the present application, the term "DMA" refers to N,N-dimethylacetamide.

In the present application, the term "DMSO" refers to dimethyl sulfoxide.

In the present application, the methylating agent refers to an agent capable of introducing a methyl group to a carbon, silicon, nitrogen, phosphorus, oxygen, or sulfur atom in a substrate molecule.

In the present application, the chlorinating agent refers to an agent capable of providing a chlorine atom and introducing it to a carbon, silicon, nitrogen, phosphorus, or sulfur atom in a substrate molecule.

In the present application, the dehydrating agent refers to an agent capable of removing water molecules in the structure of a compound under heating or in the presence of a catalyst.

In the present application, the aminating agent is an agent capable of introducing an amino group or a substituted amino group to a carbon, silicon, nitrogen, phosphorus, oxygen, or sulfur atom in a substrate molecule.

In some embodiments of the present application, the chiral compound is in an enantiomeric excess, and the enantiomeric excess means that the content (mole) of the chiral isomer therein is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In the present application, the achiral salt of the compound of Formula IV can be prepared by contacting the compound of Formula IV with the corresponding achiral acid compound in a solvent. For example, the hydrochloride of the compound of Formula IV can be prepared from the compound of Formula IV and HCl.

In the present application, the graphic representations of racemic, ambiscalemic and scalemic or enantiomerically pure compounds are from Maehr, J. Chem. Ed. 1985, 62: 114-120. Unless otherwise stated, wedged bond and dashed bond are used to denote the absolute configuration of a stereogenic center. Unless otherwise stated, when the compounds described herein contain an olefinic double bond or any other geometric asymmetry center, they include E and Z geometric isomers. Likewise, all tautomeric forms are included within the scope of the present application.

In the present application, the compounds may have specific geometric or stereoisomeric forms. The present application contemplates all such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomers- or diastereoisomers-enriched mixtures, all of which belong to the scope of the present application. The substituents such as alkyl, etc. may have additional asymmetric carbon atoms. All these isomers and mixtures thereof are included within the scope of the present application.

In the present application, the reactions are optionally carried out in a solvent. All solvents used in the present application are commercially available and can be used without further purification. The reactions are generally carried out under inert nitrogen in an anhydrous solvent.

The compounds are named by hand or ChemDraw® software and the commercially available compounds use the names in catalog provided by the suppliers.

In the present application, proton nuclear magnetic resonance data were recorded on a BRUKER AV-500 (500 MHz) spectrometer with the chemical shifts represented by (ppm) downfield from tetramethylsilane. Mass spectra were determined on Waters XEVO G2 QTOF. The mass spectrometer was equipped with an electrospray ion source (ESI) operated in a positive or negative mode.

The preparation methods according to the present application have the advantages of short steps, high stereoselectivity, high atomic utilization rate, mild reaction conditions, and simple post-treatment, and avoid the use of expensive asymmetric reaction catalysts and are suitable for industrial production.

SPECIFIC EMBODIMENTS

The following examples are provided as further detailed non-limiting illustrations of the technical solutions of the present application. They should not be construed as limiting the scope of the present application, but as merely illustrations and typical representatives of the present application. The solvents, reagents and raw materials used in the present application are all commercially available, chemically pure or analytically pure products.

Example 1: (R)-5-cyclopentylpyrazolidin-3-one D-tartrate

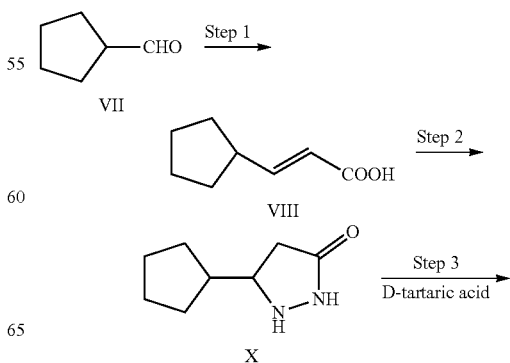

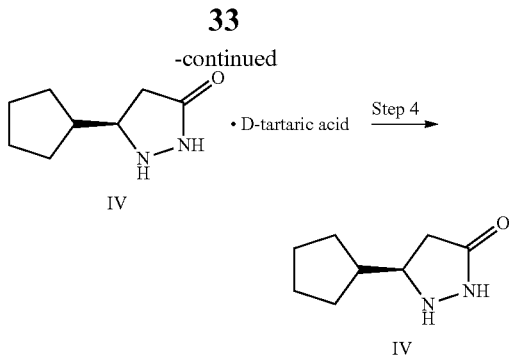

Step 1: 3-cyclopentyl Acrylic Acid 660 mL of cyclopentanecarbaldehyde and 500 g of malonic acid were added to 1 L of pyridine, and 13.4 mL of piperidine was added dropwise thereto and the resulting mixture was stirred at room temperature to react for 1 hour. Then the temperature was raised to 80° C. and the stirring was continued for 5 hours. After the reaction was completed, the resulting mixture was concentrated under reduced pressure to distill off the pyridine, and then 2.6 L of purified water was added thereto and the pH was adjusted to 2~5 with concentrated hydrochloric acid. Then, the resulting mixture was extracted with ethyl acetate (1.7 L×3), and the organic layers were combined, and washed sequentially with 1 L of water and 1 L of saturated brine. To the combined organic layer was added 4 L of 9% sodium hydroxide (1.3 L×3) and stirred, and the aqueous layers were combined and cooled down to 0~5° C., and then concentrated hydrochloric acid was added dropwise thereto to adjust the pH to 2~5 and the resulting mixture was extracted by adding 2.6 L of ethyl acetate. The aqueous layer was washed with ethyl acetate (1.3 L×2), and the organic layers were combined, washed with 2.6 L of purified water and then with 2.6 L of saturated brine, dried over anhydrous sodium sulfate, filtered, and concentrated under reduced pressure to obtain 3-cyclopentyl acrylic acid (650 g, 96.6%).

$^1$H-NMR (500 MHz, CDCl$_3$): δ=11.24 (bs, 1H), 7.08 (dd, J=15.6, 8.0 Hz, 1H), 5.81 (dd, J=15.5, 1.2 Hz, 1H), 2.64 (dd, J=8.1, 7.6 Hz, 1H), 1.92~1.81 (m, 2H), 1.71 (ddq, J=12.5, 6.5, 2.9 Hz, 2H), 1.68~1.58 (m, 2H), 1.48~1.37 (m, 2H);

MS (ES): 141.09 (M+H$^+$).

Step 2: 5-cyclopentylpyrazolidin-3-one 586 g of hydrazine hydrate was cooled down to 0~5° C., and 600 g of 3-cyclopentyl acrylic acid was added thereto under stirring. After the addition was completed, the resulting mixture was heated to 70~75° C. to react for 0.5 hour. After the reaction was completed, the reaction solution was concentrated under reduced pressure into an oil, and 1.2 L of purified water was added to dissolve the oil under stirring, and then the resulting mixture was cooled down to 0~5° C., stirred and crystallized overnight. The resulting mixture was suction-filtered and the filter cake was rinsed with 1.5 L of isopropyl ether and dried at 45° C. to obtain 5-cyclopentylpyrazolidin-3-one (508 g, 77.0%).

$^1$H-NMR (500 MHz, DMSO-d6): δ=8.92 (bs, 1H), 5.17 (bs, 1H), 3.13 (q, J=8.3 Hz, 1H), 2.32 (dd, J=15.8, 7.3 Hz, 1H), 2.03 (dd, J=15.9, 8.4 Hz, 1H), 1.89 (d, J=8.2 Hz, 1H), 1.75~1.62 (m, 2H), 1.60~1.42 (m, 4H), 1.26 (dq, J=12.4, 7.6 Hz, 1H), 1.20~1.06 (m, 1H);

MS (ES): 155.21 (M+H$^+$).

Step 3: (R)-5-cyclopentylpyrazolidin-3-one D-tartrate 406 g of the racemic 5-cyclopentylpyrazolidin-3-one was added to 4.1 L of acetone, stirred and dissolved to obtain a clear solution, and then 198 g of D-tartaric acid was added thereto. After the resulting mixture was stirred for 30 minutes, the temperature was lowered to 0~5° C. to crystallize. After filtration, the filter cake was rinsed with 1.5 L of acetone and then dried at 45° C. to obtain (R)-5-cyclopentylpyrazolidin-3-one D-tartrate (326 g, 40.7%) with an ee value of 99.4%.

Step 4: (R)-5-cyclopentylpyrazolidin-3-one 220 mL of sodium hydroxide solution (3M) was slowly dropped into (R)-5-cyclopentylpyrazolidin-3-one D-tartrate (64 g) and cooled in an ice bath to 0~5° C., and then concentrated hydrochloric acid was slowly added dropwise thereto under stirring until the solution became cloudy. Then, the pH of the solution was adjusted to neutral with 30 mL of 3M hydrochloric acid, and the resulting mixture was extracted three times with in total 500 mL of dichloromethane. The organic layers were combined, dried over anhydrous magnesium sulfate and filtered, and the filtrate was collected and concentrated under reduced pressure to obtain the product (24.71 g, 76.2%).

$^1$H-NMR (500 MHz, DMSO-d6): δ=8.93 (bs, 1H), 5.15 (bs, 1H), 3.17 (q, J=7.9 Hz, 1H), 2.30 (dd, J=16.0, 7.3 Hz, 1H), 2.01 (dd, J=16.0, 8.4 Hz, 1H), 1.89 (m, 1H), 1.74~1.60 (m, 2H), 1.55 (m, 2H), 1.47 (m, 2H), 1.26 (m, 1H), 1.14 (m, 1H);

MS (ES): 155.12 (M+H$^+$).

Example 2: (R)-3-cyclopentyl-3-(4-(7H-pyrrolo[2,3-d]pyrimidin-4-yl)-1H-pyrazol-1-yl)propionitrile

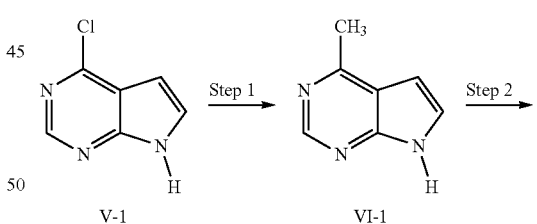

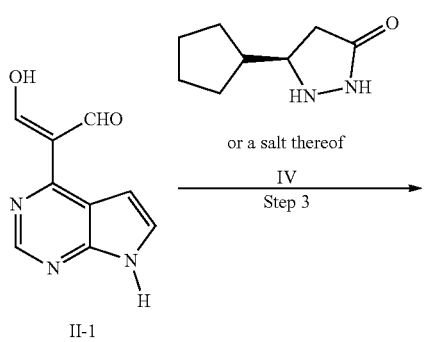

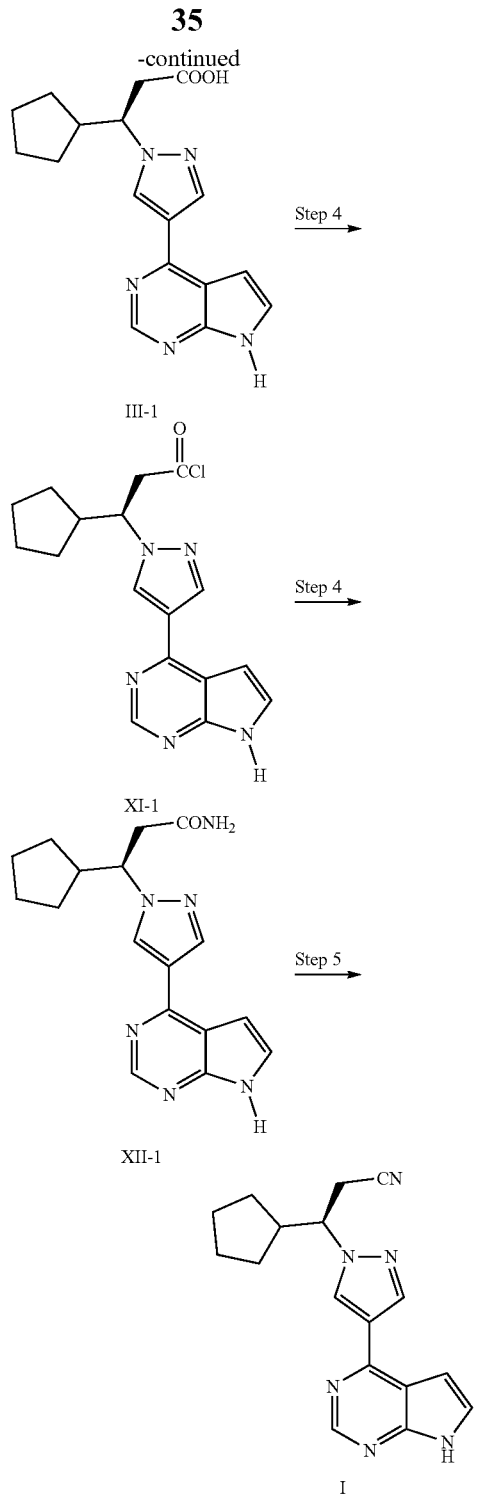

Step 1: 4-methyl-7H-pyrrolo[2,3-d]pyrimidine 150 g of 4-chloro-7H-pyrrolo[2,3-d]pyrimidine and 5.72 g of Pd(bppf)Cl₂ were added to 1.5 L of tetrahydrofuran, stirred at room temperature for 0.5 hour, and then cooled down to below 0° C. To the resulting mixture was slowly added dropwise 850 mL of methylmagnesium bromide (3M dissolved in ether). After the addition was completed, the temperature was raised to 6065° C., and the resulting mixture reacted under reflux for 2 hours. Then, the temperature was lowered to below 0° C., and the reaction was quenched by slowly adding dropwise concentrated hydrochloric acid. After the addition was completed, 650 mL of purified water was added to the resulting mixture and stirred for 15 minutes, the phases were separated and the organic phase was discarded. The aqueous phase was adjusted to pH 6 with NaHCO₃ and then suction-filtered, the filter cake was washed with 455 mL of purified water, and the filtrate was collected and extracted three times with 1.05 L of ethyl acetate, and then the organic phase was concentrated to obtain 4-methyl-7H-pyrrolo[2,3-d]pyrimidine (109.5 g, 84.2%).

$^1$H-NMR (500 MHz, DMSO-d6): δ=12.00 (bs, 1H), 8.61 (s, 1H), 7.47 (d, J=3.6 Hz, 1H), 6.62 (d, J=3.5 Hz, 1H), 2.64 (d, J=1.6 Hz, 3H);

MS (ES): 134.07 (M+H$^+$).

Step 2: 3-hydroxy-2-(7H-pyrrolo[2,3-d]ipyrimidin-4-yl)acrylaldehyde 91.6 g of 4-methyl-7H-pyrrolo[2,3-d]pyrimidine was added to a mixed solvent of 230 mL of DMF and 460 mL of dioxane and cooled down to below 0° C., and then 190 mL of phosphorus oxychloride was added dropwise thereto under stirring, and the temperature of the solution was kept to be lower than 20° C. After the addition was completed, the resulting mixture was heated to 80° C. and stirred to react for 3 hours, and then concentrated under reduced pressure to remove dioxane and DMF. To the residue was added 920 mL of tetrahydrofuran, and the pH was adjusted to 10~12 with 25% aqueous NaOH solution. After the addition was completed, the resulting mixture was heated to 60° C. and stirred to react for 2 hours. Then, the mixture was adjusted to pH 6-7 with concentrated hydrochloric acid, cooled, stirred and crystallized for 2 hours, and then suction-filtered to obtain a filter cake. The filter cake was dried at 60° C. to obtain 3-hydroxy-2-(7H-pyrrolo[2,3-d]pyrimidin-4-yl)acrylaldehyde (78.3 g, 60.2%).

$^1$H-NMR (500 MHz, DMSO-d6): δ=13.51 (bs, 1H), 12.04 (bs, 1H), 9.49 (s, 2H), 8.72 (s, 1H), 7.47 (dd, J=46.2, 3.7 Hz, 2H);

MS (ES): 190.06 (M+H$^+$).

Step 3: (R)-3-(4-(7H-pyrrolo[2,3-d]pyrimidin-4-yl)-1H-pyrazol-1-yl)-3-cyclopentylpropionic acid Method I: 54 g of 3-hydroxy-2-(7H-pyrrolo[2,3-d]pyrimidin-4-yl) acrylaldehyde was added to a mixed solvent of 648 mL of acetic acid and 324 mL of purified water, and then 87 g of (R)-5-cyclopentylpyrazolidin-3-one D-tartrate was added thereto. The resulting mixture was heated to reflux to react for 8 hours. After the reaction was completed, the reaction solution was concentrated under reduced pressure, and to the residue was added 500 mL of water, the pH was adjusted to 6.5~7, and then the resulting solution was washed twice with 300 mL of ethyl acetate. The aqueous phase was further adjusted to pH 5~5.5 with 3M HCl and suction-filtered to obtain (R)-3-(4-(7H-pyrrolo[2,3-d]pyrimidin-4-yl)-1H-pyrazol-1-yl)-3-cyclopentylpropionic acid (55.8 g, 60.0%).

Method 5 g of 3-hydroxy-2-(7H-pyrrolo[2,3-d]pyrimidin-4-yl)acrylaldehyde was added to 100 mL of water, and then 1.3 g of sodium hydroxide and 4.1 g of (R)-5-cyclopentylpyrazolidin-3-one were added thereto. The resulting mixture was heated to reflux to react for 8 hours. After the reaction was completed, the resulting mixture was adjusted to pH 1~2 with hydrochloric acid, concentrated under reduced pressure, and then dissolved in 100 mL of methanol. Then 1.4 g of sodium methoxide was added to the resulting mixture, heated to reflux for 0.5 h and concentrated to dryness, and the residue was refined with ethyl acetate for 2 h and then suction-filtered to obtain sodium (R)-3-(4-(7H-pyrrolo[2,3-d]pyrimidin-4-yl)-1H-pyrazol-1-yl)-3-cyclopentylpropionate (6.7 g, 73.0%).

Method III: 10.1 g of 3-hydroxy-2-(7H-pyrrolo[2,3-d]pyrimidin-4-yl) acrylaldehyde was added into 200 mL of anhydrous ethanol, and then 8.23 g of (R)-5-cyclopentylpyrazolidin-3-one was added thereto. The resulting mixture was heated to reflux to react for 36 hours. After the reaction was completed, the resulting mixture was concentrated under reduced pressure to distill off the solvent, and then 120 g of 2M NaOH solution was added to the residue and stirred at room temperature for 5 h, and the pH was adjusted to 6~7 with 3M HCl. Then, 200 mL of ethyl acetate was added to wash the resulting mixture three times, and the aqueous phase was further adjusted to pH 5~5.5 with 3M HCl and then extracted three times with 400 mL of ethyl acetate. The organic layers were combined and concentrated to dryness to obtain (R)-3-(4-(7H-pyrrolo[2,3-d]pyrimidin-4-yl)-1H-pyrazol-1-yl)-3-cyclopentylpropionic acid (11.3 g, 65.7%).

$^1$H-NMR (500 MHz, DMSO-d6): δ=12.12 (bs, 1H), 8.66 (s, 2H), 8.28 (s, 1H), 7.56 (s, 1H), 6.98 (s, 1H), 4.68~4.39 (m, 1H), 2.99 (t, J=13.0 Hz, 1H), 2.84 (d, J=16.6 Hz, 1H), 2.43~0.89 (m, 10H);

MS (ES): 326.16 (M+H$^+$).

Step 4: (R)-3-(4-(7H-pyrrolo[2,3-d]pyrimidin-4-yl)-1H-pyrazol-1-yl)-3-cyclopentylpropionamide 48 g of (R)-3-(4-(7H-pyrrolo[2,3-d]pyrimidin-4-yl)-1H-pyrazol-1-yl)-3-cyclopentylpropionic acid was added to a mixed solvent of 48 mL of dichloromethane and 80 mL of NMP, and then 48 mL of oxalyl chloride was added dropwise thereto, and the temperature during this process was kept not higher than 5° C. After the addition was completed, the resulting mixture reacted for 2.5 hours at a temperature maintained at 20~25° C. The above reaction solution was then dropped into an appropriate amount of aqueous ammonia and reacted for 1 hour. After the reaction was completed, the resulting mixture was concentrated under reduced pressure to remove the dichloromethane, the aqueous phase was extracted with ethyl acetate (800 mL×3), and the resulting organic phase was concentrated under reduced pressure to remove the ethyl acetate to obtain (R)-3-(4-(7H-pyrrolo[2,3-d]pyrimidin-4-yl)-1H-pyrazol-1-yl)-3-cyclopentylpropionamide (29.8 g, 62%).

$^1$H-NMR (500 MHz, DMSO-d6): δ=12.06 (bs, 1H), 8.67 (s, 1H), 8.58 (s, 1H), 8.28 (s, 1H), 7.56 (d, J=3.6 Hz, 1H), 7.35 (d, J=3.1 Hz, 1H), 6.98 (d, J=3.6 Hz, 1H), 6.79 (d, J=3.1 Hz, 1H), 4.59 (td, J=9.7, 3.9 Hz, 1H), 2.90 (dd, J=15.3, 10.0 Hz, 1H), 2.73~2.62 (m, 2H), 1.84 (dddd, J=40.6, 13.1, 8.0, 4.6 Hz, 2H), 1.56~1.24 (m, 6H);

MS (ES): 325.18 (M+H$^+$).

Step 5: (R)-3-cyclopentyl-3-(4-(7H-pyrrolo[2,3-d]pyrimidin-4-yl)-1H-pyrazol-1-yl)propionitrile 14.6 g of (R)-3-(4-(7H-pyrrolo[2,3-d]pyrimidin-4-yl)-1H-pyrazol-1-yl)-3-cyclopentylpropionamide was added to a mixed solvent of 480 mL of dichloromethane and 40 mL of NMP, and then 28 mL of phosphorus oxychloride was added dropwise thereto. The reaction was performed at room temperature, the temperature during this process was kept not higher than 30° C., and the reaction was carried out for 3 hours. After the reaction was completed, to the reaction solution was added 600 mL of purified water, and then a saturated sodium bicarbonate solution was added dropwise until the pH of the mixture solution was 7. The mixture solution was layered, and the organic phase was concentrated under reduced pressure to obtain (R)-3-cyclopentyl-3-(4-(7H-pyrrolo[2,3-d]pyrimidin-4-yl)-1H-pyrazol-1-yl) propionitrile (10.6 g, 77.3%).

$^1$H-NMR (500 MHz, DMSO-d6): δ=12.13 (bs, 1H), 8.84 (d, J=0.4 Hz, 1H), 8.69 (s, 1H), 8.37 (s, 1H), 7.63 (dd, J=2.3, 3.5 Hz, 1H), 7.01 (dd, J=1.4, 3.4 Hz, 1H), 4.56 (td, J=19.5, 4.6 Hz, 1H), 3.26 (dd, J=17.3, 9.9 Hz, 1H), 3.17 (dd, J=17.4, 4.3 Hz, 1H), 2.43 (m, 1H), 1.83 (m, 1H), 1.64~1.09 (m, 7H);

MS (ES): 307.17 (M+H$^+$).

Example 3: 4-chloro-7-((2-(trimethylsilyl)ethoxy)methyl)-7H-pyrrolo[2,3-d]pyrimidine

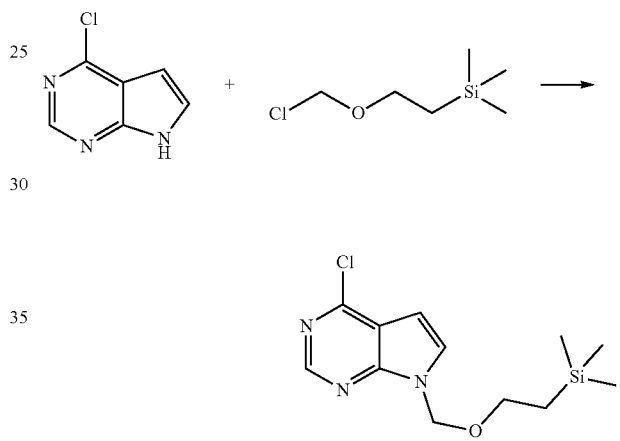

450 g of 4-chloropyrrolo[2,3-d]pyrimidine was added to 3.6 L of DMF, and the temperature was lowered to −10° C.~−20° C., and then 144 g of sodium hydride (60%) was added in batches. 586.0 g of 2-(trimethylsilyl)ethoxymethyl chloride was slowly added dropwise to the resulting mixture and stirred to react for 2 hours. After the reaction was completed, the reaction was quenched by dropwise adding 36 g of glacial acetic acid under stirring. Then, the reaction solution was poured into 14.4 L of purified water, and extracted with ethyl acetate, and then the organic layer was washed with saturated brine. The organic layer was concentrated under reduced pressure to remove the solvent, and the residue was purified by using 200300 mesh silica gel column chromatography to obtain 4-chloro-7-((2-(trimethylsilyl)ethoxy)methyl)-7H-pyrrolo[2,3-d]pyrimidine (808.2 g, 97.2%).

$^1$H-NMR (500 MHz, DMSO-d6): δ=8.69 (s, 1H), 7.85 (d, J=3.8 Hz, 1H), 6.70 (d, J=3.6 Hz, 1H), 5.62 (s, 2H), 3.53 (t, J=7.9 Hz, 2H), 0.81 (t, J=8.1 Hz, 2H), 0.23 (s, 9H);

MS (ES): 284.10 (M+H$^+$).

39

Example 4: (R)-3-cyclopentyl-3-(4-(7H-pyrrolo[2,3-d]pyrimidin-4-yl)-1H-pyrazol-1-yl)propionitrile

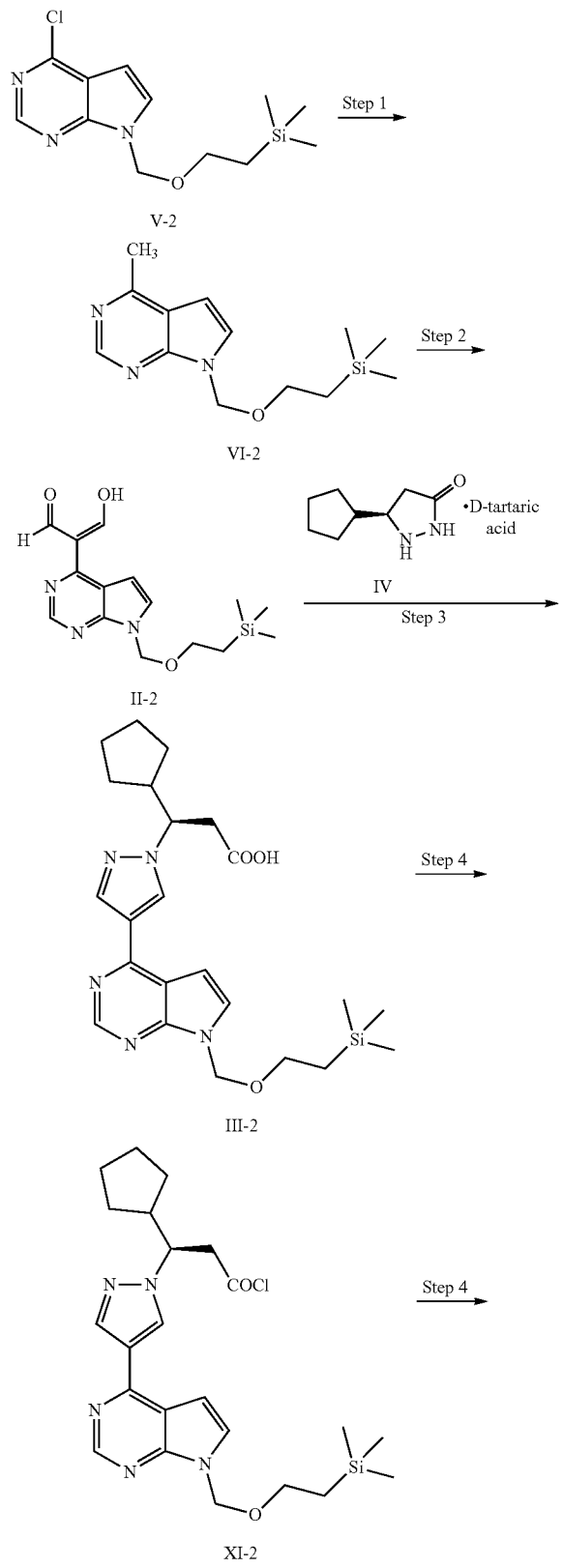

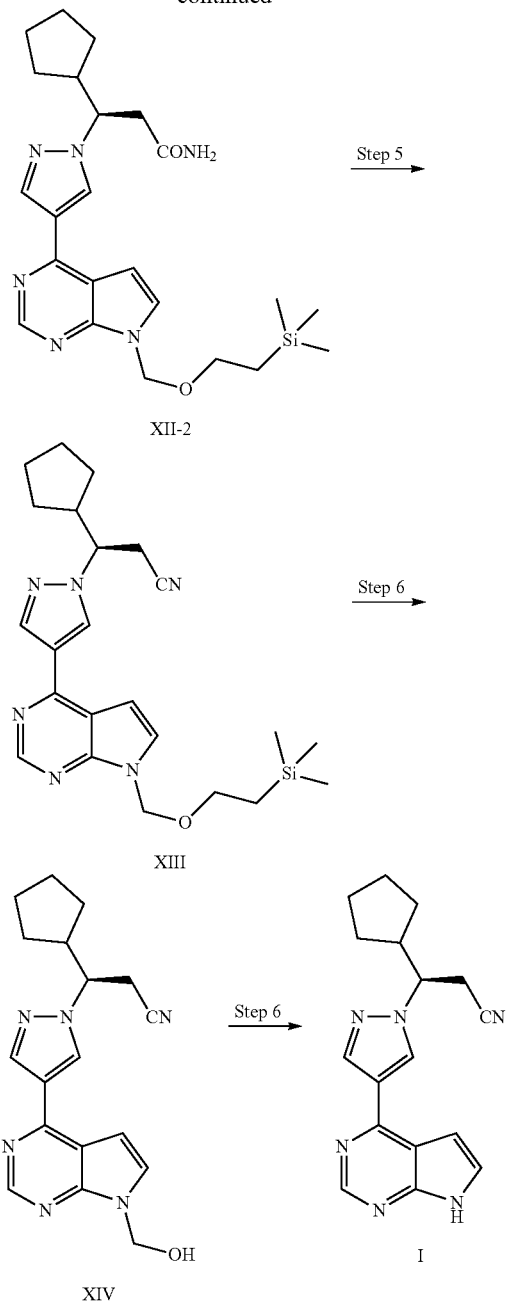

Step 1: 4-methyl-7-((2-(trimethylsilyl)ethoxy)methyl)-7H-pyrrolo[2,3-d]pyrimidine 103.6 g of 4-chloro-7-((2-(trimethylsilyl)ethoxy)methyl)-7H-pyrrolo[2,3-d]pyrimidine and 2.96 g of [1,1'-bis(diphenylphosphino)ferrocene]dichloropalladium were added to 1.13 L of tetrahydrofuran, and cooled down to −15~−5° C., and then 200 mL of methylmagnesium bromide (3M dissolved in ether) was slowly added dropwise thereto. After the addition was completed, the resulting mixture was heated to 60~65° C. and reacted under reflux for 2 hours. After the reaction was completed, the temperature was lowered to −15~−5° C., and then the reaction was quenched by slowly dropwise adding 455 mL of a saturated ammonium chloride solution. The resulting mixture was filtered, the filter cake was rinsed with 455 mL of tetrahydrofuran, and then the filter cake was discarded, and the filtrate was concentrated under reduced pressure. To the residue was added 455 mL of purified water, and 1.13 L of ethyl acetate was added to extract the resulting mixture twice. The organic phases were combined and washed with 150 g of saturated brine. Then, the organic phase was concentrated under reduced pressure to distill off the solvent to obtain 103.2 g 4-methyl-7-((2-(trimethylsilyl)ethoxy)methyl)-7H-pyrrolo[2,3-d]pyrimidine.

$^1$H-NMR (500 MHz, DMSO-d6): δ=8.67 (s, 1H), 7.63 (d, J=3.7 Hz, 1H), 6.70 (d, J=3.6 Hz, 1H), 5.60 (s, 2H), 3.54~3.45 (m, 2H), 2.64 (s, 3H), 0.81 (t, J=8.0 Hz, 2H), 0.12 (s, 9H);

MS (ES): 264.15 (M+H$^+$).

Step 2: 3-hydroxy-2-7-((2-(trimethylsilyl)ethoxy)methyl)-7H-pyrrolo[2,3-d]pyrimidin-4-yl)acrylaldehyde 103.2 g of 4-methyl-7-((2-(trimethylsilyl)ethoxy)methyl)-7H-pyrrolo[2,3-d]pyrimidine was added into 453 mL of DMF and cooled down to −15~−5° C., and then 184.2 g of phosphorus oxychloride was added dropwise thereto under stirring, and the temperature was kept at −5~5° C. After the addition was completed, the resulting mixture was heated to 80° C. and stirred to react for 3 hours. After the reaction was completed, the resulting mixture was concentrated under reduced pressure to distill off the DMF, to the residue was added 1.13 L of tetrahydrofuran, and the temperature was lowered to 0~5° C. NaOH solution was slowly added dropwise to the resulting mixture, and the temperature of the solution was kept below 20° C. After the addition was completed, the resulting mixture was heated to 60° C. and stirred to react for 2 hours. The reaction solution was concentrated under reduced pressure, adjusted to pH 4 with 3M hydrochloric acid, and then extracted twice with 1.13 L of ethyl acetate. The organic layers were combined, washed with saturated brine, dried over anhydrous sodium sulfate, and then decolorized by activated carbon. Then, the resulting mixture was filtered, and the filtrate was concentrated under reduced pressure to obtain a black sticky residue. 453 mL of anhydrous ether was added to the black sticky residue, and the temperature was raised until a clear solution was obtained, and then the resulting solution was slowly cooled down to 0~5° C., and crystallized under stirring for 4 hours. The resulting mixture was filtered, and the filter cake was rinsed twice with in total 113 mL of ether and then dried under reduced pressure to obtain 3-hydroxy-2-((4(2-((trimethylsilyl)ethoxy)methyl)-7H-pyrrolo[2,3-d]pyrimidin-4-yl) acrylaldehyde (53.2 g, 41.9%).

$^1$H-NMR (500 MHz, DMSO-d6): δ=15.77 (s, 1H), 9.51 (s, 2H), 8.80 (s, 1H), 7.70 (d, J=3.7 Hz, 1H), 7.58 (d, J=3.7 Hz, 1H), 5.63 (s, 2H), 3.55~3.48 (m, 2H), 0.83 (t, J=8.0 Hz, 2H), 0.10 (s, 9H);

MS (ES): 320.14 (M+H$^+$).

Step 3: (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionic acid 51.2 g of 3-hydroxy-2-7-((2-(trimethylsilyl)ethoxy)methyl)-7H-pyrrolo[2,3-d]pyrimidin-4-yl)acrylaldehyde was added to 2.05 L of anhydrous ethanol. After the solution was clear, 53.7 g of (R)-5-cyclopentylpyrazolidin-3-one D-tartrate was added thereto, and the resulting mixture was heated to 8085° C. and reacted under reflux for 9 hours. After the reaction was completed, the resulting mixture was concentrated under reduced pressure to distill off the solvent, and to the residue was added 640 g of 2M NaOH solution. The resulting mixture was stirred at room temperature for 1.0 hour, adjusted to pH 3~4 with 3M HCl, and then extracted twice by adding 256 mL of ethyl acetate. The organic layers were combined and washed with saturated brine. After filtration, the filtrate was concentrated under reduced pressure, and the residue was purified by using 200-300 mesh silica gel column chromatography to obtain (R)-3-cyclopentyl-3-(4-(7-((2-(trimethylsilyl)ethoxy)methyl)-7H-pyrrolo[2,3-d]pyrimidin-4-yl)-1H-pyrazol-1-yl) propionic acid (58.4 g, 79.6%).

$^1$H-NMR (500 MHz, DMSO-d6): δ=12.22 (s, 1H), 8.74 (s, 1H), 8.70 (s, 1H), 8.31 (s, 1H), 7.74 (d, J=3.7 Hz, 1H), 7.09 (d, J=3.7 Hz, 1H), 5.63 (s, 2H), 4.55 (td, J=9.9, 3.7 Hz, 1H), 3.52 (t, J=8.0 Hz, 2H), 3.04 (dd, J=16.5, 10.3 Hz, 1H), 2.89 (dd, J=16.4, 3.7 Hz, 1H), 2.35 (d, J=8.5 Hz, 1H), 1.81 (dtd, J=11.0, 6.9, 3.7 Hz, 1H), 1.62~1.47 (m, 3H), 1.31~1.21 (m, 3H), 0.83 (t, J=8.0 Hz, 2H), 0.10 (s, 9H);

MS (ES): 456.24 (M+H$^+$).

Step 4: (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionamide 49.2 g of (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionic acid was added to 480 mL of dichloromethane, and then 16.59 mL of oxalyl chloride was added dropwise thereto. After the addition was completed, 0.1 mL of DMF was added to the resulting mixture and reacted at 20~25° C. for 3 hours. The reaction solution was then dropped into 480 mL of aqueous ammonia and reacted for 1 hour. After the reaction was completed, the resulting mixture was concentrated under reduced pressure to remove the dichloromethane. The aqueous phase was extracted three times with ethyl acetate (450 mL×3) and the resulting organic phase was concentrated under reduced pressure to remove the ethyl acetate to obtain (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionamide (48 g, 97.5%).

$^1$H-NMR (500 MHz, DMSO-d6): δ=8.73 (s, 1H), 8.61 (s, 1H), 8.29 (s, 1H), 7.74 (d, J=3.7 Hz, 1H), 7.34 (d, J=2.6 Hz, 1H), 7.08 (d, J=3.6 Hz, 1H), 6.76 (d, J=2.5 Hz, 1H), 5.63 (s, 2H), 4.59 (td, J=9.7, 3.9 Hz, 1H), 3.53 (t, J=8.0 Hz, 2H), 2.89 (dd, J=15.3, 10.0 Hz, 1H), 2.66 (dd, J=15.3, 3.9 Hz, 1H), 2.36 (q, J=8.4 Hz, 1H), 1.81 (dtd, J=11.6, 7.1, 3.7 Hz, 1H), 1.62~1.48 (m, 3H), 1.46~1.37 (m, 1H), 1.26 (td, J=14.9, 13.6, 7.9 Hz, 3H), 0.83 (t, J=8.0 Hz, 2H), 0.10 (d, J=1.7 Hz, 9H);

MS (ES): 455.26 (M+H$^+$).

Step 5: (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionitrile 200 mL of dichloromethane was added to 42.6 g of (R)-3-cyclopentyl-3-(4-(7-((2-(trimethylsilyl)ethoxy)methyl)-7H-pyrrolo[2,3-d]pyrimidin-4-yl)-1H-pyrazol-1-yl) propionamide, and then 57 mL of phosphorus oxychloride was added dropwise thereto and the resulting mixture reacted at room temperature for 24 hours. After the reaction was completed, to the resulting mixture was added 300 mL of purified water, and a saturated sodium bicarbonate solution was added dropwise until the pH of the mixture solution was 7. The mixture solution was layered, and the organic phase was concentrated under reduced pressure to obtain (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionitrile (38.4 g, 93.8%).

$^1$H-NMR (500 MHz, DMSO-d6): δ=8.83 (s, 1H), 8.75 (s, 1H), 8.39 (s, 1H), 7.77 (d, J=3.7 Hz, 1H), 7.09 (d, J=3.7 Hz, 1H), 5.63 (s, 2H), 4.53 (td, J=9.4, 4.0 Hz, 1H), 3.51 (t, J=8.1 Hz, 2H), 3.23 (dq, J=9.3, 4.3 Hz, 2H), 2.41 (m, 1H), 1.79 (m, 1H), 1.66~1.13 (m, 7H), 0.81 (t, J=8.2 Hz, 2H), 0.124 (s, 9H);

MS (ES): 437.25 (M+H$^+$).

Step 6: (R)-3-cyclopentyl-3-(4-(7H-pyrrolo[2,3-d]pyrimidin-4-yl)-1H-pyrazol-1-yl)propionitrile 35 g of (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionitrile was added to 700 mL of acetonitrile, and then 31.5 mL of boron trifluoride ethyl ether was added dropwise thereto. After the addition was completed, the resulting mixture was heated to 60~70° C. and reacted for 5 hours, and then 270 mL of aqueous ammonia and 540 mL of purified water were added thereto and stirred at room temperature for 12 hours. After the reaction was completed, to the reaction solution were added 200 mL of ethyl acetate and 200 mL of saturated ammonium chloride, the aqueous phase was extracted three times with ethyl acetate (300 mL×3), and the organic phase was concentrated under reduced pressure to obtain (R)-3-cyclopentyl-3-(4-(7H-pyrrolo[2,3-d]pyrimidin-4-yl)-1H-pyrazol-1-yl) propionitrile (22.61 g, 92.1%).

$^1$H-NMR (500 MHz, DMSO-d6): δ=12.10 (bs, 1H), 8.80 (d, J=0.4 Hz, 1H), 8.68 (s, 1H), 8.37 (s, 1H), 7.60 (dd, J=2.3, 3.5 Hz, 1H), 6.99 (dd, J=1.4, 3.4 Hz, 1H), 4.53 (td, J=9.5, 4.3 Hz, 1H), 3.26 (dd, J=17.3, 9.9 Hz, 1H), 3.19 (dd, J=17.4, 4.3 Hz, 1H), 2.39 (m, 1H), 1.82 (m, 1H), 1.60~1.08 (m, 7H);

MS (ES): 307.17 (M+H$^+$).

Example 5: (R)-3-(4-(7H-pyrrolo[2,3-d]pyrimidin-4-yl)-1H-pyrazol-1-yl)-3-cyclopentylpropionamide

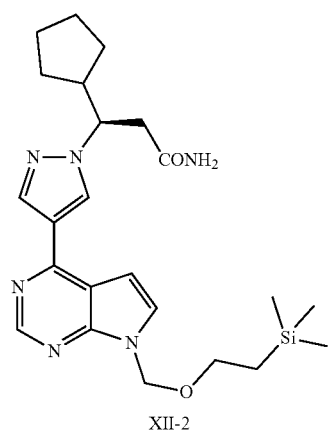

XII-2

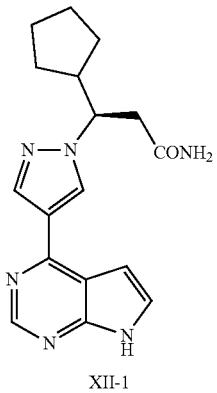

XII-1

6.0 g of (R)-3-cyclopentyl-3-(4-(7-((2-(trimethylsilyl)ethoxy)methyl)-7H-pyrrolo[2,3-d]pyrimidin-4-yl)-1H-pyrazol-1-yl)propionamide was added to 120 mL of acetonitrile, and then 6 mL of boron trifluoride ethyl ether was added dropwise thereto. After the addition was completed, the resulting mixture was heated to 60~70° C. and reacted for 7 hours, and then 60 mL of aqueous ammonia and 54 mL of purified water were added thereto and stirred at room temperature for 6 hours. After the reaction was completed, to the reaction solution were added 60 mL of ethyl acetate and 50 mL of saturated sodium chloride, the aqueous phase was extracted three times with ethyl acetate (60 mL×3), and the organic phase was concentrated under reduced pressure to obtain (R)-3-(4-(7H-pyrrolo[2,3-d]pyrimidin-4-yl)-1H-pyrazol-1-yl)-3-cyclopentylpropionamide (4.08 g, 95.3%).

$^1$H-NMR (500 MHz, DMSO-d6): δ=12.06 (bs, 1H), 8.66 (s, 1H), 8.58 (s, 1H), 8.29 (s, 1H), 7.56 (d, J=3.6 Hz, 1H), 7.33 (d, J=3.1 Hz, 1H), 6.97 (d, J=3.6 Hz, 1H), 6.79 (d, J=3.1 Hz, 1H), 4.55 (td, J=9.7, 3.9 Hz, 1H), 2.90 (dd, J=15.3, 10.0 Hz, 1H), 2.72~2.62 (m, 2H), 1.84 (dddd, J=40.6, 13.1, 8.0, 4.6 Hz, 2H), 1.55~1.24 (m, 6H);

MS (ES): 325.11 (M+H$^+$).

Example 6: (R)-3-(4-(7H-pyrrolo[2,3-d]pyrimidin-4-yl)-1H-pyrazol-1-yl)-3-cyclopentylpropionamide

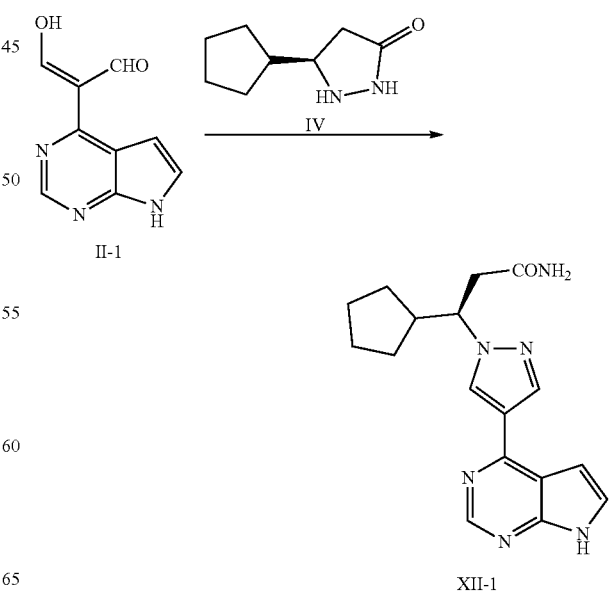

3-hydroxy-2-(7H-pyrrolo[2,3-d]pyrimidin-4-yl)acrylaldehyde (30.1 g) was added to a mixed solvent of 180 mL of tetrahydrofuran and 180 mL of aqueous ammonia to obtain a clear solution, and then 29.4 g (R)-5-cyclopentylpyrazolidin-3-one was added thereto. After the addition was completed, the resulting mixture was reacted for 10 hours at a temperature maintained at 60~70° C., and then water (1.2 L) was added thereto and the resulting mixture was extracted with ethyl acetate (1.8 L×3). Then, the ethyl acetate was removed by concentrating under reduced pressure to obtain a concentrate (50.4 g). The concentrate was heated under reflux and refined for 1 h in acetonitrile, slowly cooled down, and stirred at 0~5° C. for 1 h. The resulting mixture was suction-filtered to obtain a red-brown solid, and a crude product (33.2 g) was obtained by collecting with a yield of 64.4%. The crude product was heated in 300 mL of isopropanol and dissolved to obtain a clear solution. Then, the resulting solution was cooled, stirred and crystallized, and then suction-filtered to obtain (R)-3-(4-(7H-pyrrolo[2,3-d]pyrimidin-4-yl)-1H-pyrazol-1-yl)-3-cyclopentylpropionamide (15.3 g, 46.1%, purity>99.4%).

$^1$H-NMR (500 MHz, DMSO-d6): δ=12.04 (bs, 1H), 8.67 (s, 1H), 8.56 (s, 1H), 8.26 (s, 1H), 7.54 (d, J=3.6 Hz, 1H), 7.33 (d, J=3.1 Hz, 1H), 6.96 (d, J=3.6 Hz, 1H), 6.77 (d, J=3.1 Hz, 1H), 4.57 (td, J=9.7, 3.9 Hz, 1H), 2.90 (dd, J=15.3, 10.0 Hz, 1H), 2.71~2.63 (m, 2H), 1.82 (dddd, J=40.6, 13.1, 8.0, 4.6 Hz, 2H), 1.54~1.22 (m, 6H);

MS (ES): 325.18 (M+H$^+$).

What is claimed is:

1. A process for preparing ruxolitinib, a compound of Formula I, comprising the following steps:

Step 3: reacting a compound of Formula II with a compound of Formula IV or a salt thereof to obtain a compound of Formula III,

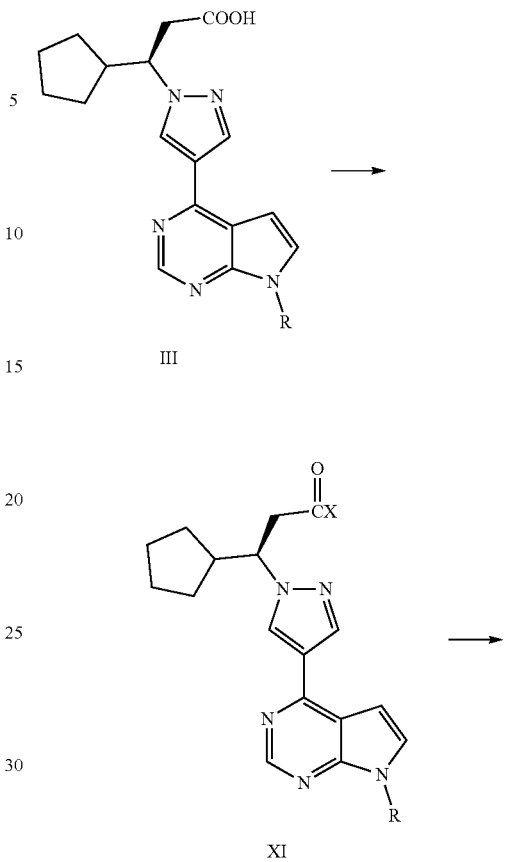

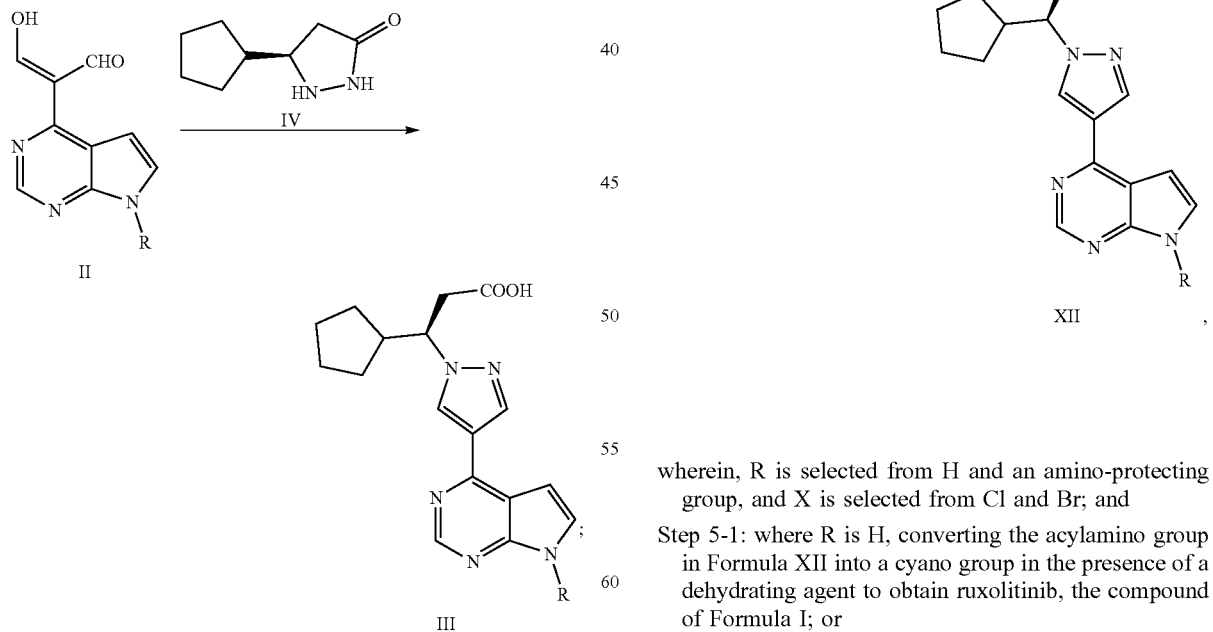

Step 4: converting the compound of Formula III into a compound of Formula XI, and then converting the compound of Formula XI into a compound of Formula XII in the presence of an aminating agent, wherein, R is selected from H and an amino-protecting group, and X is selected from Cl and Br; and Step 5-1: where R is H, converting the acylamino group in Formula XII into a cyano group in the presence of a dehydrating agent to obtain ruxolitinib, the compound of Formula I; or Step 5-2: where R is an amino-protecting group, converting the acylamino group in Formula XII into a cyano group in the presence of a dehydrating agent and removing the amino-protecting group R to obtain ruxolitinib, the compound of Formula I;

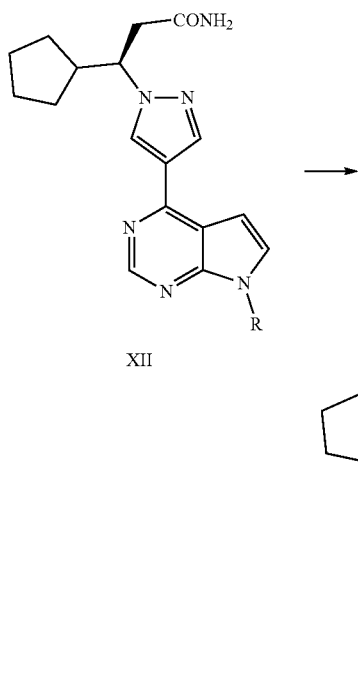

XII

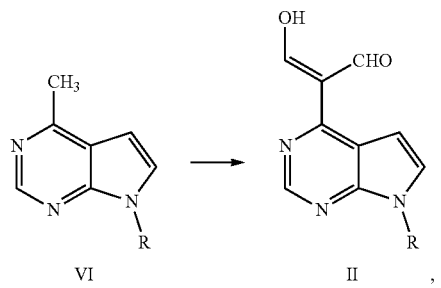

I wherein, R is selected from H and an amino-protecting group, wherein, the reagent used in the reaction of converting the compound of Formula III into the compound of Formula XI in Step 4 is selected from one or more of phosphorus trichloride, phosphorus pentachloride, thionyl chloride and oxalyl chloride; and wherein, the aminating agent used in the reaction of converting the compound of Formula XI into the compound of Formula XII in Step 4 is selected from one or more of aqueous ammonia, liquid ammonia, and ammonia gas.

2. The process according to claim 1, further comprising Step 2: converting a compound of Formula VI into the compound of Formula II in the presence of DMF and a chlorinating agent,

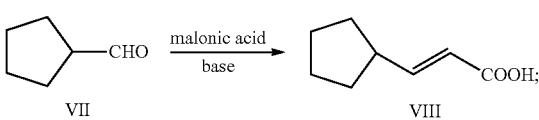

wherein, R is selected from H and an amino-protecting group; and wherein, the chlorinating agent in Step 2 is selected from oxalyl chloride, phosphorus oxychloride, thionyl chloride, and a mixture of any two or more of the above agents.

3. The process according to claim 1, wherein the process for preparing the compound of Formula IV or a chiral salt thereof in Step 3 comprises the following steps:

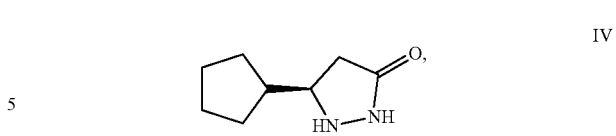

Step C-1: reacting a compound of Formula X with a chiral acid in the presence of a solvent to form a chiral salt of the compound of Formula IV,

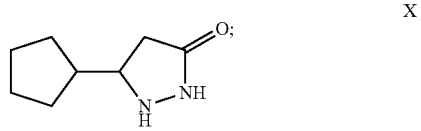 [SMILES: O=C1CC(C2CCCC2)NN1]

Step C-2: separating the chiral salt of the compound of Formula IV; and

Step C-3: optionally, treating the chiral salt of the compound of Formula IV with a base to obtain the compound of Formula IV.

4. The process according to claim 3, wherein the process for preparing the compound of Formula IV or a chiral salt thereof in Step 3 further comprises the following steps:

Step A: reacting a compound of Formula VII with malonic acid in the presence of a base to obtain a compound of Formula VIII,

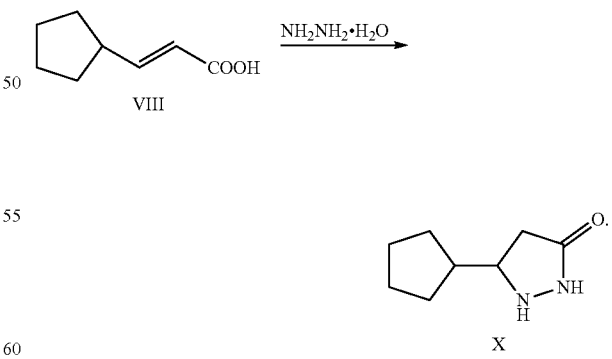

and

Step B: reacting the compound of Formula VIII with hydrazine hydrate to obtain the compound of Formula X, 5. A process for preparing ruxolitinib, a compound of Formula I, comprising the following steps:

Step (1): reacting a compound of Formula II with a compound of Formula IV or a salt thereof in the presence of $NH_3$ to obtain a compound of Formula XII,

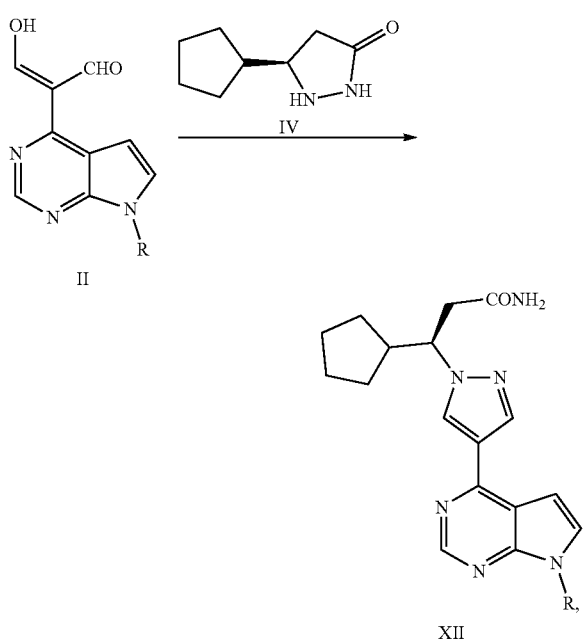

wherein, R is selected from H and an amino-protecting group; and

Step (2-1): where R is H, converting the acylamino group in Formula XII into a cyano group in the presence of a dehydrating agent to obtain ruxolitinib, the compound of Formula I, or Step (2-2): where R is an amino-protecting group, converting the acylamino group in Formula XII into a cyano group in the presence of a dehydrating agent and removing the amino-protecting group R to obtain ruxolitinib, the compound of Formula I;

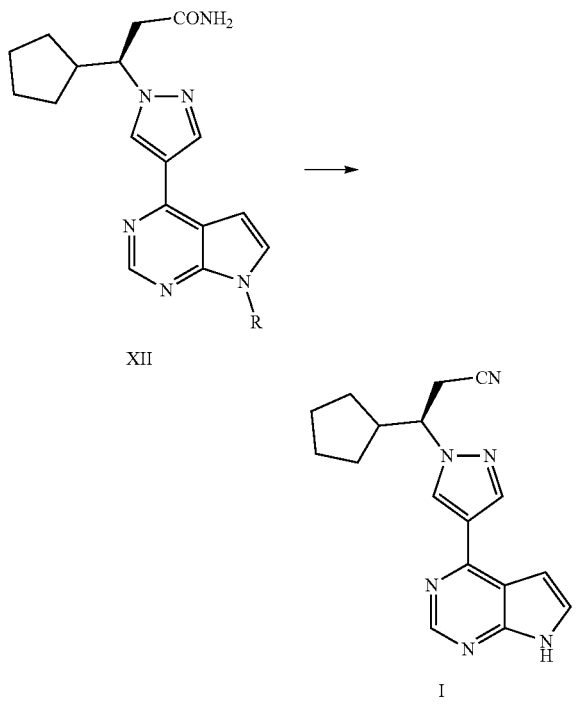

wherein, R is selected from H and an amino-protecting group.

6. The process according to claim 1, wherein the amino-protecting group is selected from benzyloxycarbonyl, 2,2,2-trichloroethoxycarbonyl, 2-(trimethylsilyl)ethoxycarbonyl, 2-(4-trifluoromethylphenylsulfonyl)ethoxycarbonyl, tert-butoxycarbonyl, 1-adamantyloxycarbonyl, 2-adamantylcarbonyl, 2,4-dimethylpent-3-yloxycarbonyl, cyclohexyloxycarbonyl, 1,1-dimethyl-2,2,2-trichloroethoxycarbonyl, vinyl, 2-chloroethyl, 2-phenylsulfonylethyl, p-nitrophenylsulfonyl, p-toluenesulfonyl, phenyl sulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl, benzyloxymethyl, 2-tetrahydropyranyl, tri($C_{1-4}$alkyl)silyl, 1,1-diethoxymethyl, 2-(trimethylsilyl)ethoxymethyl and N-pivaloyloxymethyl.

7. The process according to claim 5, wherein the amino-protecting group is selected from benzyloxycarbonyl, 2,2,2-trichloroethoxycarbonyl, 2-(trimethyl silyl)ethoxycarbonyl, 2-(4-trifluoromethylphenylsulfonyl)ethoxycarbonyl, tert-butoxycarbonyl, 1-adamantyloxycarbonyl, 2-adamantylcarbonyl, 2,4-dimethylpent-3-yloxycarbonyl, cyclohexyloxycarbonyl, 1,1-dimethyl-2,2,2-trichloroethoxycarbonyl, vinyl, 2-chloroethyl, 2-phenylsulfonylethyl, p-nitrophenylsulfonyl, p-toluenesulfonyl, phenyl sulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butoxymethyl, benzyloxymethyl, 2-tetrahydropyranyl, tri($C_{1-4}$alkyl)silyl, 1,1-diethoxymethyl, 2-(trimethylsilyl)ethoxymethyl and N-pivaloyloxymethyl.

8. The process according to claim 1, wherein Step 3 is carried out under an acidic, basic or neutral condition.

9. The process according to 8, wherein the acidic condition is provided by adding an acidic reagent selected from citric acid, fumaric acid, tartaric acid, maleic acid, malic acid, succinic acid, acetic acid, ascorbic acid, sulfuric acid, hydrochloric acid, hydrobromic acid, and a mixture thereof; and, wherein the basic condition is provided by adding an alkaline reagent selected from sodium hydroxide, potassium hydroxide, lithium hydroxide, potassium carbonate, cesium carbonate, sodium carbonate, triethylamine, diisopropylethylamine, DBU, and a mixture thereof.

10. The process according to claim 1, wherein the molar ratio of the compound of Formula II to the compound of Formula IV is 1.0:1.0~5.0.

11. The process according to claim 2, wherein the chlorinating agent in Step 2 is phosphorus oxychloride.

12. The process according to claim 6, wherein the amino-protecting group is selected from 2-(trimethylsilyl)ethoxymethyl, N-pivaloyloxymethyl, p-nitrophenyl sulfonyl, p-toluenesulfonyl, phenyl sulfonyl, methanesulfonyl or benzyl.

13. The process according to claim 12, wherein the amino-protecting group is 2-(trimethylsilyl)ethoxymethyl.

14. The process according to claim 7, wherein the amino-protecting group is selected from 2-(trimethylsilyl)ethoxymethyl, N-pivaloyloxymethyl, p-nitrophenyl sulfonyl, p-toluenesulfonyl, phenyl sulfonyl, methanesulfonyl or benzyl.

15. The process according to claim 14, wherein the amino-protecting group is 2-(trimethylsilyl)ethoxymethyl.

16. The process according to 10, wherein the acidic condition is provided by adding an acidic reagent selected from tartaric acid, acetic acid or hydrochloric acid.

17. The process according to 9, wherein the basic condition is provided by adding an alkaline reagent selected from triethylamine, sodium hydroxide or potassium hydroxide.

18. The process according to claim 10, wherein the molar ratio of the compound of Formula II to the compound of Formula IV is 1.0:1.0~3.0.

19. The process according to claim 18, wherein the molar ratio of the compound of Formula II to the compound of Formula IV is 1.0:1.0~1.5.

20. The process according to claim 19, wherein the molar ratio of the compound of Formula II to the compound of Formula IV is 1.0:1.0~1.2.

* * * * *